United States Patent
Gentz et al.

(10) Patent No.: US 6,238,888 B1
(45) Date of Patent: May 29, 2001

(54) KERATINOCYTE GROWTH FACTOR-2 FORMULATIONS

(75) Inventors: Reiner L. Gentz, Rockville; Arvind Chopra, Gaithersburg; Parveen Kaushal, Silver Spring, all of MD (US); Thomas Spitznagel, Vienna, VA (US); Edward Unsworth, Kensington; Fazel Khan, Gaithersburg, both of MD (US)

(73) Assignee: Human Genone Sciences, Inc., Rockville, MD (US)

( * ) Notice: Subject to any disclaimer, the term of this patent is extended or adjusted under 35 U.S.C. 154(b) by 0 days.

(21) Appl. No.: 09/218,444

(22) Filed: Dec. 22, 1998

Related U.S. Application Data

(60) Provisional application No. 60/068,493, filed on Dec. 22, 1997.

(51) Int. Cl.[7] .......................... A61K 38/18; C07K 14/50; C12N 15/18; C12N 15/63
(52) U.S. Cl. .................. 435/69.4; 435/69.1; 435/243; 435/320.1; 435/325; 514/12; 514/2; 514/925; 530/300; 530/324; 530/328; 530/399; 530/402; 536/23.51
(58) Field of Search ............................. 435/69.4, 252.33, 435/320.1, 325; 514/44; 424/93.21, 530; 536/23.5, 23.1

(56) References Cited

U.S. PATENT DOCUMENTS

| | | | |
|---|---|---|---|
| 5,194,596 | 3/1993 | Tischer et al. | 530/399 |
| 5,350,836 | 9/1994 | Kopchick et al. | 530/399 |
| 5,580,856 | 12/1996 | Prestelski et al. | 514/21 |
| 5,677,278 | 10/1997 | Gospodarowicz et al. | 514/12 |
| 5,703,047 | 12/1997 | Wilson | 514/12 |
| 5,731,170 | 3/1998 | Rubin et al. | 435/69.4 |
| 5,773,252 * | 6/1998 | Greene et al. | 435/69.4 |
| 5,773,586 | 6/1998 | Gospodarowicz et al. | 530/399 |
| 5,814,605 | 9/1998 | Pierce et al. | 514/12 |
| 5,824,643 | 10/1998 | Pierce et al. | 514/12 |
| 5,843,883 | 12/1998 | Gospodarowicz et al. | 468/547 |
| 5,863,767 | 1/1999 | Gospodarowicz et al. | 435/694 |

FOREIGN PATENT DOCUMENTS

| | | |
|---|---|---|
| 2 321 852 | 8/1998 | (GB) . |
| 7-345689 | 12/1995 | (JP) . |
| 8-103240 | 3/1996 | (JP) . |
| 8-214378 | 7/1996 | (JP) . |
| 10-330283 | 12/1998 | (JP) . |
| 10-330284 | 12/1998 | (JP) . |
| 10-330285 | 12/1998 | (JP) . |
| WO 90/08771 | 8/1990 | (WO) . |
| WO 92/14480 | 9/1992 | (WO) . |
| WO 92/22304 | 12/1992 | (WO) . |
| WO 93/21908 | 11/1993 | (WO) . |
| WO 94/22427 | 10/1994 | (WO) . |
| WO 94/23032 | 10/1994 | (WO) . |
| WO 95/01434 | 1/1995 | (WO) . |
| WO 95/03831 | 2/1995 | (WO) . |
| WO 95/24928 | 9/1995 | (WO) . |
| WO 96/11949 | 4/1996 | (WO) . |
| WO 96/11950 | 4/1996 | (WO) . |
| WO 96/11951 | 4/1996 | (WO) . |
| WO 96/11952 | 4/1996 | (WO) . |
| WO 96/22369 | 7/1996 | (WO) . |
| WO 96/25422 | 8/1996 | (WO) . |
| WO 97/20929 | 12/1997 | (WO) . |
| WO 98/06844 | 2/1998 | (WO) . |
| WO 98/16243 | 4/1998 | (WO) . |
| WO 98/16642 | 4/1998 | (WO) . |

OTHER PUBLICATIONS

Finch, P. W. et al., "Human KGF Is FGF–Related with Properties of a Paracrine Effector of Epithelial Cell Growth," *Science* 245:752–755 (1989).

Hartung, H. et al., "Murine FGF–12 and FGF–13: expression in embryonic nervous sytem, connective tissue and heart," *Mech. Develop.* 64:31–39 (Jun. 1997).

Hartung, H. et al., "Assignment[a] of Fgf12 to mouse chromosome bands 16B1→B3 in situ hybridization," *Cytogenet. Cell Genet.* 76:185–186 (Apr. 1997).

Jimenez, P. et al., "Effect of Topical Keratinocyte Growth Factor–2 on Wound Healing In A Glucocorticoid–Impaired Model," *J. Cutan. Pathol.* 24:105 (Feb. 1997).

Jimenez, P.A. et al., "Effect of Keratinocyte Growth Factor–2 on Cell Proliferation In Vivo," *FASEB J.* 11:AS23, Abstract No. 3025 (Apr. 1997).

Kelley, M. J. et al., "Emergence of the keratinocyte growth factor multigene family during the great ape radiation," *Proc. Natl. Acad. Sci. USA* 89:9287–9291 (1992).

Mason, I. J. et al., "FGF–7 (keratinocyte growth factor) expression during mouse development suggests roles in myogenesis, forebrain regionalisation and epithelial–mesenchymal interactions," *Mech. Dev.* 45:15–30 (1994).

Miyamoto, M. et al., "Molecular Cloning of a Novel Cytokine cDNA Encoding the Ninth Member of the Fibroblast Growth Factor Family, Which Has a Unique Secretion Property," *Mol. Cell. Biol.* 13(7):4251–4259 (1993).

Ron, D. et al., "Expression of Biologically Active Recombinant Keratinocyte Growth Factor," *J. Biol. Chem.* 268(4):2984–2988 (1993).

Yamasaki, M. et al., "Structure and Expression of the Rat mRNA Encoding a Novel Member of the Fibroblast Growth Factor Family," *J. Biol. Chem.* 271:15918–15921 (Jul. 1996).

Yan, G. et al., "Sequence of Rat Keratinocyte Growth Factor (Heparin–Binding Growth Factor Type 7)," *In Vitro Cell.*

(List continued on next page.)

Primary Examiner—Karen Cochrane Carlson
Assistant Examiner—Patricia Robinson
(74) *Attorney, Agent, or Firm*—Sterne, Kessler, Goldstein & Fox P.L.L.C.

(57) ABSTRACT

The invention is directed to liquid and lyophilized forms of Keratinocyte Growth Factor-2 (KGF-2) and derivatives thereof. This invention further relates to the formulation of KGF-2 for therapeutic use, for example, to promote or accelerate wound healing.

81 Claims, 8 Drawing Sheets

OTHER PUBLICATIONS

Dev. Biol. 27A:437–438 (1991).
NCBI Entrez, GenBank Report with Revision History, Accession No. M79878, McCombie, W.R. et al. (1992).
NCBI Entrez, GenBank Report with Revision History, Accession No. T52063, Hillier, L. et al. (1995).
NCBI Entrez, GenBank Report with Revision History, Accession No. D46201, Sasaki, T. et al. (1995).
NCBI Entrez, GenBank Report with Revision History, Accession No. D46420, Sasaki, T. et al. (1995).
NCBI Entrez, GenBank Report with Revision History, Accession No. D54216, Fujiwara, T. et al. (1995).
NCBI Entrez, GenBank Report with Revision History, Accession No. D68729, Kohara, Y. et al. (1995).
NCBI Entrez, GenBank Report with Revision History, Accession No. D69248, Kohara, Y. et al. (1995).
NCBI Entrez, GenBank Report with Revision History, Accession No. D65627, Kohara, Y. et al. (1995).
NCBI Entrez, GenBank Report with Revision History, Accession No. D66221, Kohara, Y. et al. (1995).
NCBI Entrez, GenBank Report with Revision History, Accession No. C02000, Okubo, K. (Jul. 1996).
NCBI Entrez, GenBank Report with Revision History, Accession No. W29377, Marra, M. et al. (Sep. 1996).
NCBI Entrez, GenBank Report with Revision History, Accession No. W32720, Hillier, L. et al. (Oct. 1996).
NCBI Entrez, GenBank Report with Revision History, Accession No. W60824, Hillier, L. et al. (Oct. 1996).
NCBI Entrez, GenBank Report with Revision History, Accession No. T70682, Shen, B. et al. (Oct. 1996).
NCBI Entrez, GenBank Report with Revision History, Accession No. AA094753, Liew, C.C. (Oct. 1996).
NCBI Entrez, GenBank Report with Revision History, Accession No. AA133331, Hillier, L. et al. (Nov. 1996).
NCBI Entrez, GenBank Report with Revision History, Accession No. AA190058, Marra, M. et al. (Jan. 1997).
NCBI Entrez, GenBank Report with Revision History, Accession No. AA018953, Hillier, L. et al. (Jan. 1997).
NCBI Entrez, GenBank Report with Revision History, Accession No. AA240978, Marra, M. et al. (Mar. 1997).
NCBI Entrez, GenBank Report with Revision History, Accession No. AA289560, Marra, M. et al. (Apr. 1997).
NCBI Entrez, GenBank Report with Revision History, Accession No. AA296993, Adams, M.D. et al. (Apr. 1997).
NCBI Entrez, GenBank Report with Revision History, Accession No. AA298937, Adams, M.D. et al. (Apr. 1997).
NCBI Entrez, GenBank Report with Revision History, Accession No. AA312184, Adams, M.D. et al. (Apr. 1997).
NCBI Entrez, GenBank Report with Revision History, Accession No. AA312483, Adams, M.D. et al. (Apr. 1997).
NCBI Entrez, GenBank Report with Revision History, Accession No. AA356781, Adams, M.D. et al. (Apr. 1997).
NCBI Entrez, GenBank Report with Revision History, Accession No. AA412789, Marra, M. et al. (May 1997).
NCBI Entrez, GenBank Report with Revision History, Accession No. AA472256, Marra, M. et al. (Jun. 1997).
NCBI Entrez, GenBank Report with Revision History, Accession No. C38464, Kohara, Y. et al. (Sep. 1997).
NCBI Entrez, GenBank Report with Revision History, Accession No. C56505, Kohara, Y. et al. (Sep. 1997).
NCBI Entrez, GenBank Report with Revision History, Accession No. C57074, Kohara, Y. et al. (Sep. 1997).
NCBI Entrez, GenBank Report with Revision History, Accession No. C58558, Kohara, Y. et al. (Sep. 1997).
NCBI Entrez, GenBank Report with Revision History, Accession No. C58846, Kohara, Y. et al. (Sep. 1997).
NCBI Entrez, GenBank Report with Revision History, Accession No. C59317, Kohara, Y. et al. (Sep. 1997).
NCBI Entrez, GenBank Report with Revision History, Accession No. C59311, Kohara, Y. et al. (Sep. 1997).
NCBI Entrez, GenBank Report with Revision History, Accession No. AA605609, Clark, M. et al. (Sep. 1997).
NCBI Entrez, GenBank Report with Revision History, Accession No. AA621871, NCI–CGAP (Oct. 1997).
NCBI Entrez, GenBank Report with Revision History, Accession No. AA621888, NCI–CGAP (Oct. 1997).
NCBI Entrez, GenBank Report with Revision History, Accession No. AA675470, Marra, M. et al. (Nov. 1997).
NCBI Entrez, GenBank Report with Revision History, Accession No. AA675519, Marra, M. et al. (Nov. 1997).
NCBI Entrez, GenBank Report with Revision History, Accession No. AA838994, Marra, M. et al. (Feb. 1998).
NCBI Entrez, GenBank Report with Revision History, Accession No. H35048, Lee, N.H. et al. (Apr. 1998).
NCBI Entrez, GenBank Report with Revision History Accession No. AA906051, NCI–CGAP (May 1998).
NCBI Entrez, GenBank Report with Revision History Accession No. C78836, Ko, M.S.H. et al. (Jun. 1998).
English language translation of WO 97/20929 (Document AO4).
English language translation of JP 10–330283 (Document AO5).
English language translation of JP 10–330284 (Document AP5).
English language translation of JP 10–330285 (Document AL6).
English language translation of JP 7–345689 (Document AP2).
English language translation of JP 8–103240 (Document AL3).
English language translation of JP 8–214378 (Document AL4).
Jimenez et al., Direct Submission Human Genome Sciences, Aug. 25, 1996.*

* cited by examiner

ATGTGGAAATGGATACTGACACATTGTGCCTCAGCCTTTCCCCACCTGCCCCGGCTGCTGC     60
    1 ---+---+---+---+---+---+---+---+---+---+---+---+
      TACACCTTTACCTATGACTGTGTAACACGGAGTCGGAAAGGGGTGGACGGGCCGACGACG

M   W   K   W   I   L   T   H   C   A   S   A   F   P   H   L   P   G   C   C

TGCTGCTGCTTTTTGTTGCTGTCTTGGTGTCTTCCGTCCCTGTCACCTGCCAAGCCCTT    120
   61 ---+---+---+---+---+---+---+---+---+---+---+---+
      ACGACGACGAAAAACAACGACAGAACCACAGAAGGCAGGGACAGTGGACGGTTCGGGAA

C   C   C   F   L   L   L   F   L   V   S   S   V   P   V   T   C   Q   A   L

GGTCAGGAGGACATGGTGTCACCAGAGGCCACCAACTCTTCTTCCTCCTCCTTCTCCTCCT    180
  121 ---+---+---+---+---+---+---+---+---+---+---+---+
      CCAGTCCTCCTGTACCACAGTGGTCTCCGGTGGTTGAGAAGAAGGAGGAGGAAGAGGAGGA

G   Q   D   M   V   S   P   E   A   T   N   S   S   S   S   S   F   S   S   P

TCCAGGCGCGGGAAGGCATGTGCGGAGCTACAATCACCTTCAAGGAGATGTCCGCTGGAGA    240
  181 ---+---+---+---+---+---+---+---+---+---+---+---+
      AGGTCCGCGCCCTTCCGTACACGCCTCGATGTTAGTGGAAGTTCCTCTACAGGCGACCTCT

S   S   A   G   R   H   V   R   S   Y   N   H   L   Q   G   D   V   R   W   R

MATCH WITH FIG.1B

FIG.1A

MATCH WITH FIG.1A

```
     AAGCTATTCTCTTTCACCAAGTACTTTCTCAAGATTGAGAAGAACGGGAAGGTCAGCGGG
241  ------+---------+---------+---------+---------+---------+    300
     TTCGATAAGAGAAAGTGGTTCATGAAAGAGTTCTAACTCTTCTTGCCCTTCCAGTCGCCC

K  L  F  S  F  T  K  Y  F  L  K  I  E  K  N  G  K  V  S  G

ACCAAGAAGGAGAACTGCCCGTACAGCATCCTGGAGATAACATCAGTAGAAATCGGAGTT
301  ------+---------+---------+---------+---------+---------+    360
     TGGTTCTTCCTCTTGACGGGCATGTCGTAGGACCTCTATTGTAGTCATCTTTAGCCTCAA

T  K  K  E  N  C  P  Y  S  I  L  E  I  T  S  V  E  I  G  V

GTTGCCGTCAAAGCCATTAACAGCAACTATTACTTAGCCATGAACAAGAAGGGAAACTC
361  ------+---------+---------+---------+---------+---------+    420
     CAACGGCAGTTTCGGTAATTGTCGTTGATAATGAATCGGTACTTGTTCTTCCCCTTTGAG

V  A  V  K  A  I  N  S  N  Y  Y  L  A  M  N  K  K  G  K  L

TATGGCTCAAAAGAATTTAACAATGACTGTAAGCTGAAGGAGAGGATAGAGGAAAATGGA
421  ------+---------+---------+---------+---------+---------+    480
     ATACCGAGTTTTCTTAAATTGTTACTGACATTCGACTTCCTCTCCTATCTCCTTTTACCT

Y  G  S  K  E  F  N  N  D  C  K  L  K  E  R  I  E  E  N  G
```

MATCH WITH FIG.1C

FIG.1B

MATCH WITH FIG.1B

481 TACAATACCTATGCATCATTTAACTGGCAGCATAATGGGAGGCAAATGTATGTGGCATTG 540
    ----+----+----+----+----+----+----+----+----+----+----+----+
    ATGTTATGGATACGTAGTAAATTGACCGTCGTATTACCCTCCGTTTACATACACCGTAAC

Y  N  T  Y  A  S  F  N  W  Q  H  N  G  R  Q  M  Y  V  A  L

541 AATGGAAAAGGAGCTCCAAGGAGAGGACAGAAAACACGAAGGAAAAACACCTCTGCTCAC 600
    ----+----+----+----+----+----+----+----+----+----+----+----+
    TTACCTTTTCCTCGAGGTTCCTCTCCTGTCTTTTGTGCTTCCTTTTTGTGGAGACGAGTG

N  G  K  G  A  P  R  R  G  Q  K  T  R  R  K  N  T  S  A  H

601 TTTCTTCCAATGGTGGTACACTCATAG 627
    ----+----+----+----+----+--
    AAAGAAGGTTACCACCATGTGAGTATC

KERATINOCYTE GROWTH FACTOR-2 FORMULATIONS

This application claims the benefit of priority of the filing date of Provisional Application No. 60/068,493 filed on Dec. 22, 1997, which is incorporated by reference herein in its entirety.

BACKGROUND OF THE INVENTION

1. Field of the Invention

The present invention is directed to liquid and lyophilized formulations of Keratinocyte Growth Factor-2 (KGF-2) and derivatives thereof. This invention further relates to formulations of KGF-2, especially topical and injectable formulations, that can be employed for therapeutic use in indications requiring soft-tissue growth and regeneration.

2. Related Art

The fibroblast growth factor family has emerged as a large family of growth factors involved in soft-tissue growth and regeneration. It presently includes several members that share a varying degree of homology at the protein level, and that, with one exception, appear to have a similar broad mitogenic spectrum, i.e., they promote the proliferation of a variety of cells of mesodermal and neuroectodermal origin and/or promote angiogenesis.

KGF was originally identified as a member of the FGF family by sequence homology or factor purification and cloning. Keratinocyte growth factor (KGF) was isolated as a mitogen from a cultured murine keratinocyte line (Rubin, J. S. et al., *Proc. Natl. Acad. Sci. USA* 86:802–806 (1989)). Unlike the other members of the FGF family, it has little activity on mesenchyme-derived cells but stimulates the growth of epithelial cells. Keratinocyte growth factor is produced by fibroblasts derived from skin and fetal lung (Rubin et al. (1989)). The Keratinocyte growth factor mRNA was found to be expressed in adult kidney, colon and ilium, but not in brain or lung (Finch, P. W. et al. Science 245:752–755 (1989)). KGF displays the conserved regions within the FGF protein family. KGF binds to the FGF-2 receptor with high affinity.

Impaired wound healing is a significant source of morbidity and may result in such complications as dehiscence, anastomotic breakdown and, non-healing wounds. In the normal individual, wound healing is achieved uncomplicated. In contrast, impaired healing is associated with several conditions such as diabetes, infection, immunosuppression, obesity and malnutrition (Cruse, P. J. and Foord, R., *Arch. Surg.* 107:206 (1973); Schrock, T. R. et al., *Ann. Surg.* 177:513 (1973); Poole, G. U., Jr., *Surgery* 97:631 (1985); Irvin, G. L. et al., *Am. Surg* 51:418 (1985)).

Wound repair is the result of complex interactions and biologic processes. Three phases have been described in normal wound healing: acute inflammatory phase, extracellular matrix and collagen synthesis, and remodeling (Peacock, E. E., Jr., *Wound Repair*, 2nd edition, W B Saunders, Philadelphia (1984)). The process involves the interaction of keratinocytes, fibroblasts and inflammatory cells at the wound site.

It is desirable to formulate polypeptides that are capable of promoting and enhancing soft-tissue growth and regeneration in pharmaceutical compositions that (1) are stable over prolonged periods of storage, (2) increase the pharmacological activity or effectiveness of the the polypeptide and/or (3) allow facile application or administration of the polypeptide in therapeutic regimens.

SUMMARY OF THE INVENTION

The present invention is directed to liquid and lyophilized formulations of KGF-2 and deletion or point or substitution mutants thereof(referred to herein as KGF-2 polypeptides). This invention further relates to the use of such formulations of KGF-2 polypeptides to promote or accelerate soft tissue growth or regeneration, for example in wound healing, or in treating mucocytis or inflammatory bowel disease. Preferred formulations of the present invention employ novel mutant forms of KGF-2, and in one embodiment employ a deletion mutant referred to herein as KGF2-Δ33. The co-ingredients employed in the formulations (1) provide storage stability to the KGF-2 polypeptide, (2) further enhance soft-tissue healing activity of the therapeutic composition, and/or (3) provide the KGF-2 polypeptide in an active form while allowing facile application and administration for particular therapeutic purposes.

A first aspect of the present invention relates to a formulation comprising a KGF-2 polypeptide and a buffering agent having a buffering capacity of between about pH 5.0 and about pH 8.0. Useful buffers include phosphate, acetate, aconitate, succinate, malate, carbonate and citrate buffers, citrate being preferred.

A second aspect of the invention relates to a formulation comprising a KGF-2 polypeptide, a lyophilization bulking agent and a buffering agent having a buffering capacity of between about pH 5.0 and about pH 8.0. Useful buffers include phosphate, aconitate, succinate, malate, carbonate and citrate buffers, citrate being preferred.

A third aspect of the invention relates to a formulation comprising a KGF-2 polypeptide and a thiol-containing compound, preferably monothioglycerol, capable of stabilizing the KGF-2 polypeptide. This formulation preferably includes a buffering agent having a buffering capacity of between about pH 5.0 and about pH 8.0. This formulation may also include one or more antioxidants and or one or more metal chelating agents.

A fourth aspect of the present invention relates to a formulation comprising a KGF-2 polypeptide, a buffer, and a high molecular weight compound that causes the formulation to gel at a certain predefined temperature. A preferred high molecular weight compound is a Pluronic or Poloxamer polyoxyethylene-polyoxypropylene block copolymer. A thiol-containing compound, such as monothioglycerol, can be included in the formulation to provide added stability to the polypeptide.

A fifth aspect of the present invention relates to a formulation comprising a KGF-2 polypeptide, a buffering agent and a thickening agent. Thickening agents are used to increase the viscosity of the formulation. Preferred thickening agents are carboxymethyl cellulose (CMC), hydroxyethyl cellulose (HEC), hydroxypropylmethyl cellulose (HPMC), Natrosol, and Carbomers.

In addition, the formulations of the present invention may also include metal chelating agents, antioxidants or thiol-containing compounds, such as ascorbic acid ester, monothioglycerol, cystein, tocopherols, butylated hydroxyanisole, sodium sulphate, sodium bisulfite, and sodium metasulfite and preservatives such as phenol, chlorobutane, benzylalcohol, methyl parabens and propyl parabens. The formulations of the present invention may also have an nitrogen blanket overlay on the head space of the vial. Additionally, the formulations of the present invention may be include purging the formulation buffer with helium, argon, or nitrogen.

BRIEF DESCRIPTION OF THE FIGURES

FIGS. 1A–1C illustrate the cDNA and corresponding deduced amino acid sequence of KGF-2. The initial 35 or 36 amino acid residues represent the putative leader sequence (underlined). The standard one letter abbreviations for amino acids are used. Sequencing inaccuracies are a common problem when attempting to determine polynucleotide sequences. Sequencing was performed using a 373 Automated DNA sequencer (Applied Biosystems, Inc.). Sequencing accuracy is predicted to be greater than 97% accurate. (SEQ ID NOs: 1 and 2)

Figure 2A:
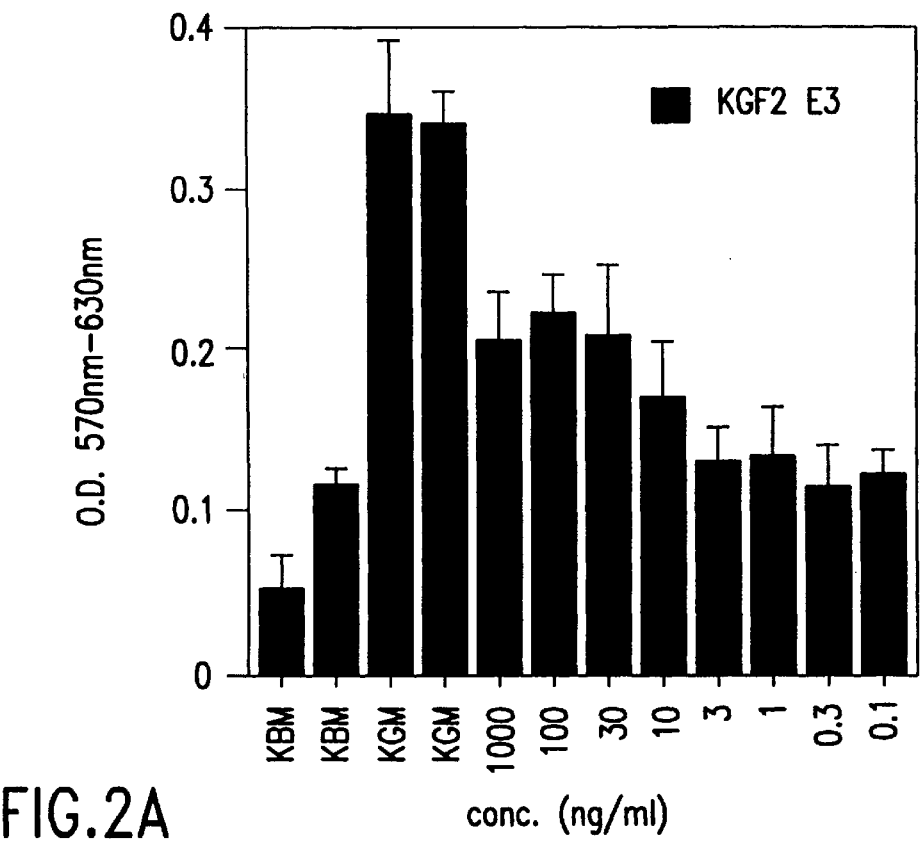
Figure 2B:
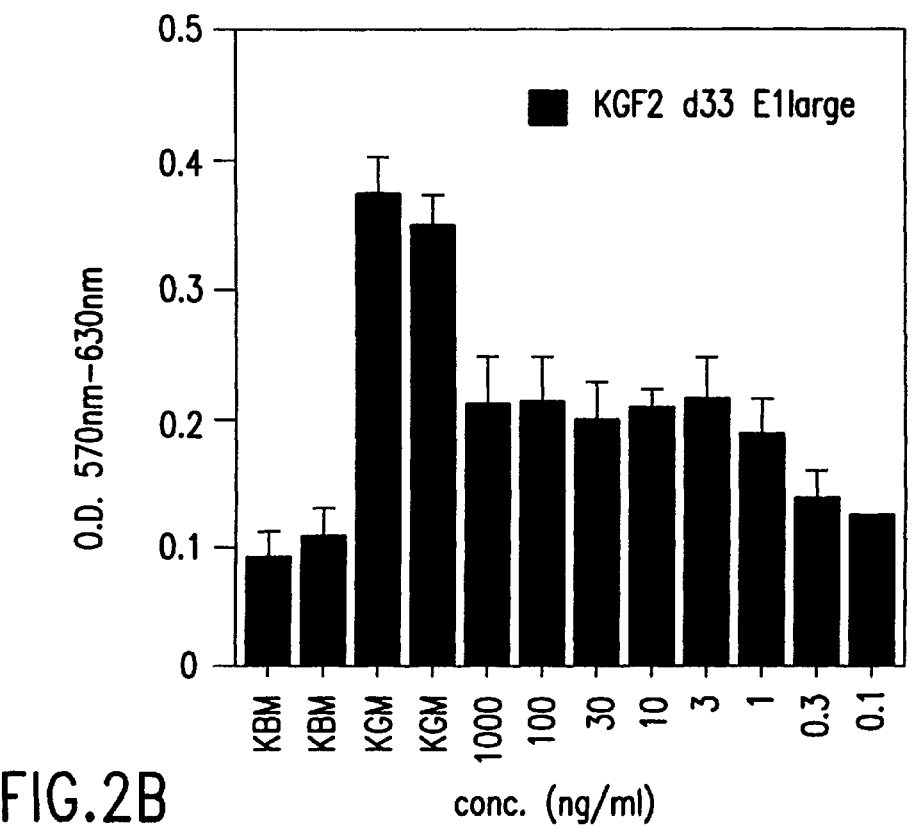
Figure 2C:
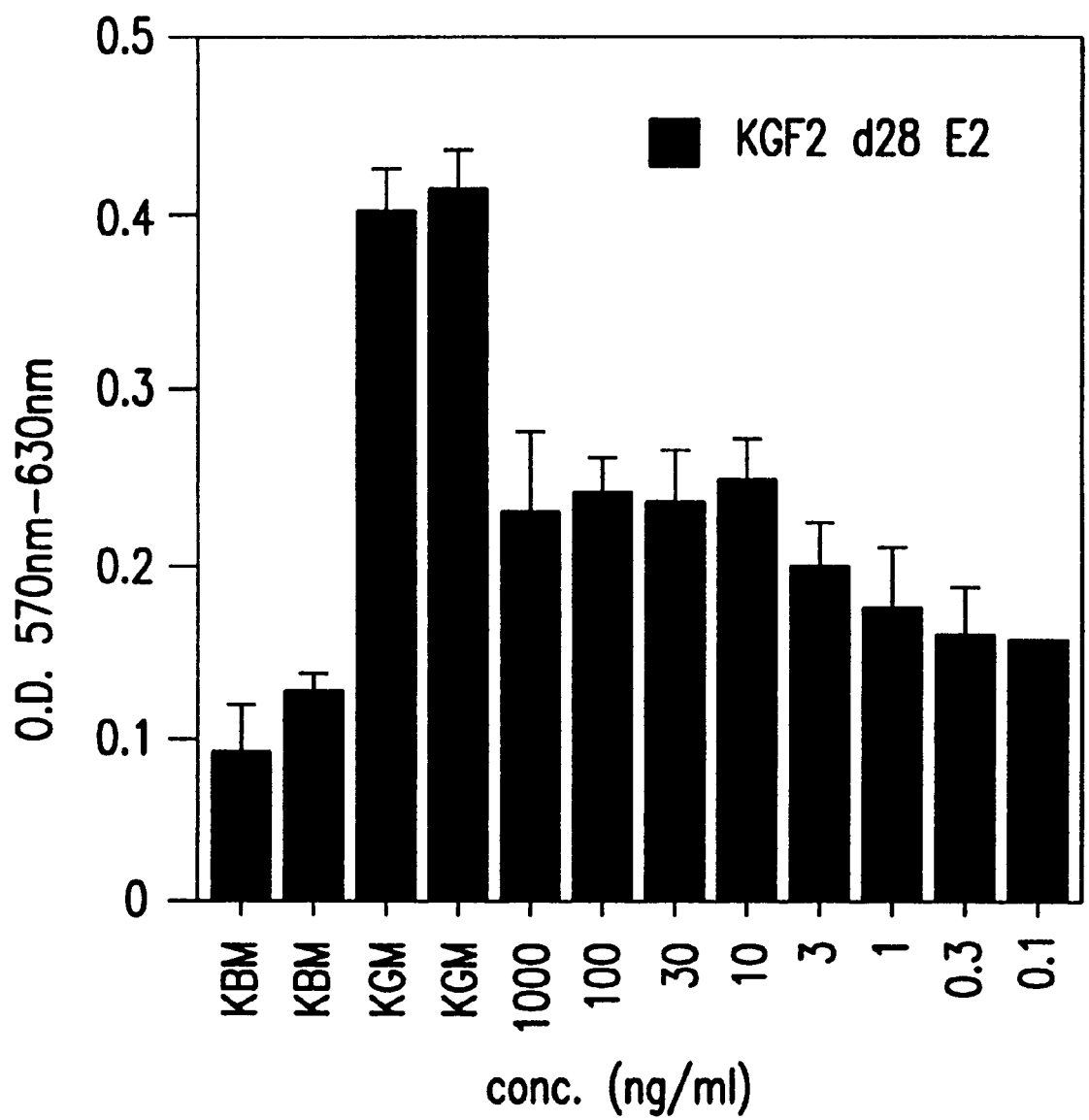

FIGS. 2(A)–2(C) depict stimulation of normal primary epidermal keratinocyte proliferation by KGF-2 polypeptides of the invention. FIG. 2(A) shows stimulation of normal primary epidermal keratinocyte proliferation by KGF-2. FIG. 2(B) shows the stimulation of normal primary epidermal keratinocyte proliferation by KGF-2 Δ33. FIG. 2(C) shows the stimulation of normal primary epidermal keratinocyte proliferation by KGF-2 Δ28.

Figure 3:
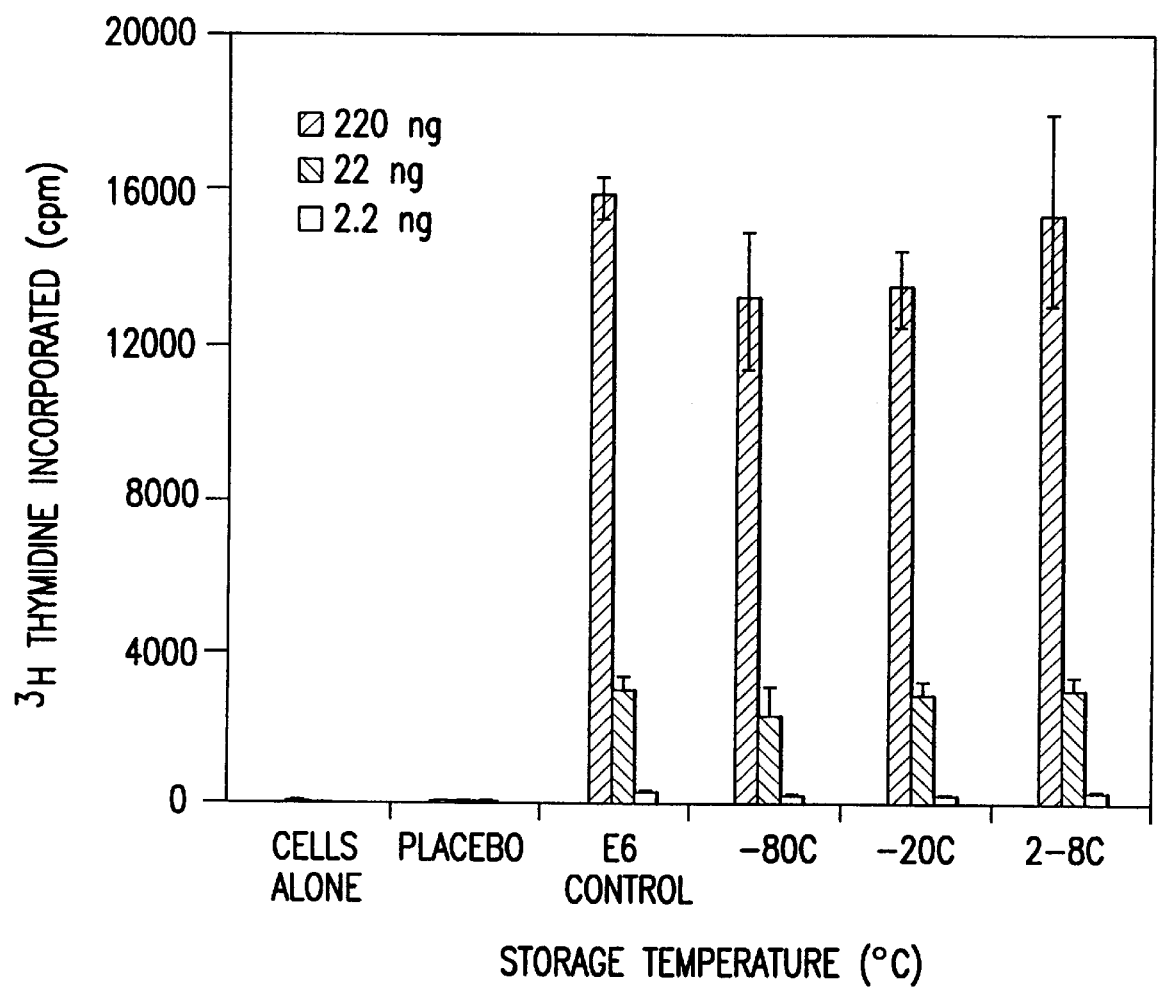

FIG. 3 shows bioactivity results for KGF-2 Δ33 liquid formulation, 10 month stability.

Figure 4:
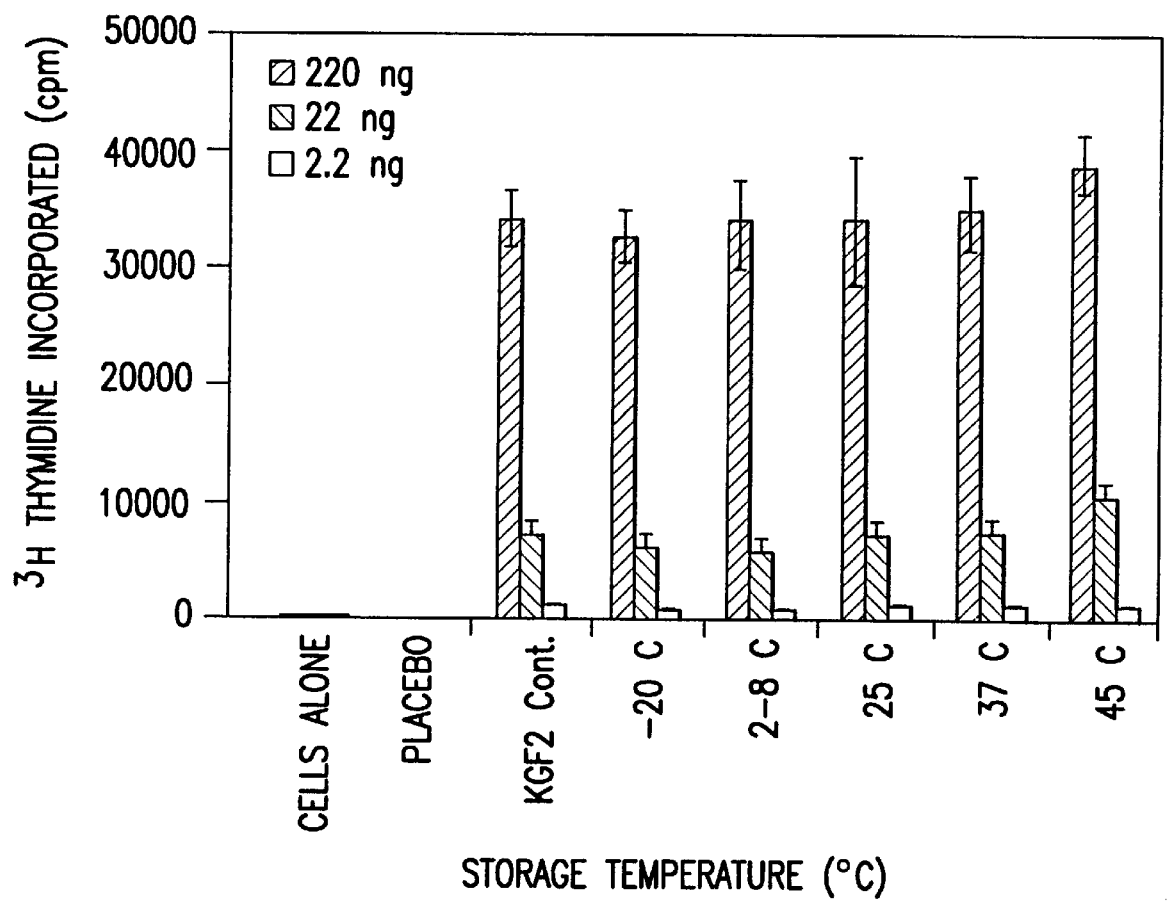

FIG. 4 shows bioactivity results for KGF-2 Δ33 lyophilized preparation, 9 month stability.

Figure 5:
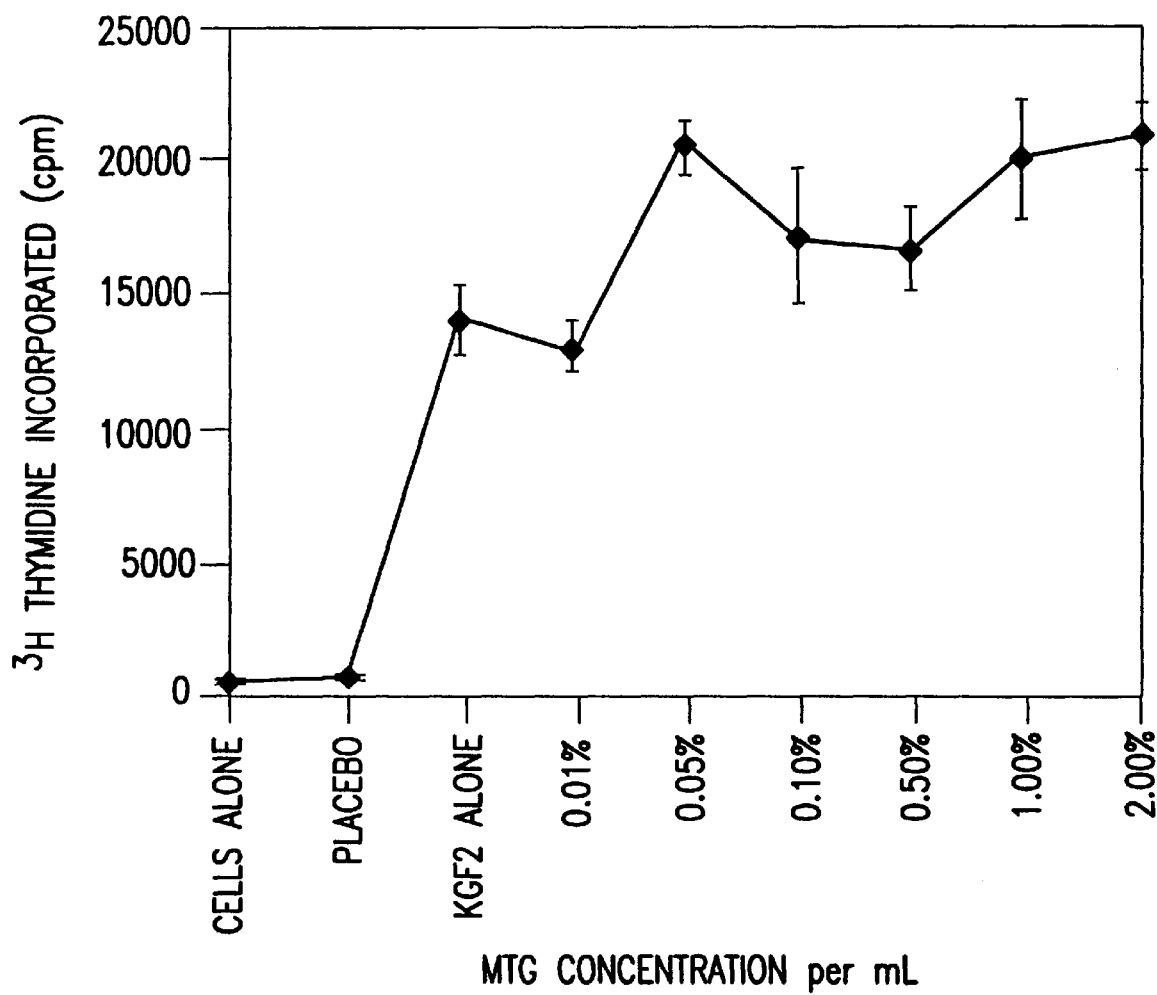

FIG. 5 shows the effect of monothiolglycerol on KGF-2 bioactivity.

DETAILED DESCRIPTION OF THE PREFERRED EMBODIMENTS

KGF-2 stimulates the proliferation of epidermal keratinocyes but not mesenchymal cells such as fibroblasts. Thus, "a polypeptide having KGF-2 protein-like activity" includes polypeptides that exhibit the KGF-2 activity, in the keratinocyte proliferation assay set forth below and bind to FGF receptor isoforms 1-iiib and 2-iiib.

The present invention is directed to pharmaceutical and veterinary formulations of KGF-2 polypeptides. The KGF-2 polypeptides are defined herein by reference to the polypeptide of FIG. 1 (SEQ ID NO:2) or that encoded by the deposited cDNA, and include fragments, derivatives and analogs of the polypeptide of FIG. 1 (SEQ ID NO:2) or that encoded by the deposited cDNA which retain essentially the same biological function as the parent polypeptide. The polypeptides employed in the present invention may be recombinant polypeptides, natural polypeptides or synthetic polypeptides, preferably recombinant polypeptides.

It has been discovered that KGF-2 polypeptides exhibit poor activity and stability at a pH of 4.5 or less, or at a pH above about 8.0. The present inventors have discovered that KGF-2 polypeptides oxidize and precipitate. These polypeptides present a difficult challenge when attempting to formulate them for therapeutic purposes. In order to maintain physico-chemical properties and biological activity, KGF-2 polypeptides can be formulated with antioxidants, such as oxygen scavenging compounds, and/or a protein stabilizer, such as a thiol-containing compound, and/or a metal-chelating agent, such as EDTA. Stabilization, as used herein, refers to the maintenance of both physico-chemical properties and substantial biological activity of the KGF-2 polypeptides over a given time period.

The formulations according to the present invention include gel, thickened solution, solution and lyophilized forms. Formulations are also referred to herein as "pharmaceutical compositions" or "compositions."

Injectable Formulations

Liquid Formulations

A first aspect of the present invention is directed to liquid formulations of KGF-2 polypeptides that comprise: a KGF-2 polypeptide and a buffer having a buffering capacity of between about pH 5.0 and about pH 8.0, more preferably pH 5.5 to pH 6.5, most preferably pH 6.2. Useful buffers include buffers derived from phosphate, acetic, aconitic, citric, glutaric, malic, succinic and carbonic acids. Typically employed is an alkali or alkaline earth salt of one of the aformentioned acids. More preferably the buffer will be acetate or citrate, most preferably citrate. For example, the formulation may comprise a composition formed by mixing a buffering amount of citric acid or a pharmaceutically acceptable salt thereof with KGF-2 Δ33 in water. The formulation alternatively may comprise a composition formed by mixing a buffering amount of acetic acid or a pharmaceutically acceptable salt thereof with KGF-2 Δ33 in water. Preferable buffer concentrations are from about 5 mM to about 50 mM. Most preferably the acetate buffer will have a concentration of about 20 mM and the citrate buffer will be about 10 mM to about 20 mM. The formulation may also include NaCl as a tonicifier at a concentration of from about 0.01 mM to about 150 mM, most preferably at about 125 mM and a metal chelating agent, such as EDTA, at a concentration of from about 0.1 mM to about 10 mM, most preferably at about I mM Additionally, a liquid formulation of the present invention may also include one or more of (a) a stabilizing amount of an antioxidant, such as ascorbate and/or (b) a protein stabilizing amount a thiol-compound, for example monothioglycerol (MTG). Without wishing to be bound by theory, it is believed that thiol compounds such as MTG serve to protect free sulfhydryl groups present in the KGF-polypeptides.

The storage conditions for the liquid formulation are typically at about 2° C. to about 8° C. Alternatively, storage conditions are at or below −20° C. Most preferably, storage conditions are at about −20° C. Maintaining a KGF-2 liquid formulation in a frozen state limits the amount of oxidation to the polypeptide which in turn results in a stable polypeptide formulation.

Preferably, a liquid formulation comprises:
(1) a therapeutically-effective amount of a KGF-2 polypeptide;
(2) an effective amount of a buffer having a buffering capacity of between about pH 5.0 and about pH 8.0; and
(3) a pharmaceutically acceptable diluent; and
(4) optionally one or more of the following:
  (a) NaCl as a tonicifier,
  (b) a chelating agent,
  (c) a stabilizing amount of an antioxidant, and
  (d) a stabilizing amount of a protein stabilizer.

The KGF-2 polypeptide preferably is maintained in solution.

Compositions of the present invention are manufactured by admixing the above listed ingredients together, preferably in concentrations and ratios as expressed herein.

Antioxidants that can be used in the liquid formulation include ascorbic acid, tocopherols, and butylated hydroxyanisole. In addition, stabilizers that can be used in the liquid formulation also include thiols such as cysteine, methionine and thioglycerols. Chelating agents that can be employed include ethylenediamine tetraacetic acid (EDTA), or diethylenetriamine pentaacetic acid (DPTA), with EDTA being preferred.

Formulations of the present invention which include antioxidants or thiols can increase the stability of the KGF-2 polypeptides. This makes it possible to have a pharmaceutical product with a longer shelf life.

More preferred liquid formulations comprise:
(1) a KGF-2 polypeptide in a concentration range of about 0.02 to about 40 mg/ml (w/v), more preferably about 0.05 to about 30 mg/ml (w/v), even more preferably about 0.1 to about 20 mg/ml (w/v), still more preferably about 10 mg/ml (w/v), and most preferably about 0.2 to 4 mg/ml;

(2) a buffer having a buffering capacity of between about pH 5.0 and about pH 8.0 at a concentration range of about 5 mM to about 50 mM, preferably about 5 mM to about 30 mM; and (3) a pharmaceutically acceptable diluent, preferably water, to bring the composition to a designated volume.

Useful buffers for the formulations of the present invention include buffers derived from acetic, aconitic, citric, glutaric, malic, succinic, phosphate and carbonic acids. Typically employed is an alkali or alkaline earth salt of one of the aformentioned acids. Acetate and citrate buffers, such as acetic acid or a pharmaceutically acceptable salt thereof, or citric acid or a pharmaceutically acceptable salt thereof, are preferred. The preferable pH ranges for the solution formulation is from about pH 5.0 to about pH 8.0, preferably pH 5.5 to pH 6.5, and most preferably about pH 6.2. Sodium acetate or sodium citrate are the preferred buffering agents, with sodium citrate being most preferred.

To the above solution also preferably added are:

(4) a chelating agent, such as EDTA at a concentration range of about 0.1 mM to about 10 mM, more preferably at about 1 mM;

(5) NaCl at a concentration range of about 0.01 mM to about 150 mM and more preferably at about 125 mM.

Optionally, a liquid formulation may also include a protein stabilizing amount of a compound selected from the group consisting of:

(a) about 0.5% to about 2% w/v glycerol, (b) about 0.1% to about 1% w/v methionine, or (c) about 0.1% to about 2% w/v monothioglycerol.

Preferred embodiments of this aspect of the present invention include a composition formed by mixing:

(1) a KGF-2 polypeptide in a concentration of about 0.02 to about 40 mg/ml (w/v), more preferably about 0.1 to about 20 mg/ml, and most preferably about 0.2 to 4 mg/ml.

(2) 10 mM sodium citrate or 20 mM sodium acetate;

(3) 125 mM NaCl;

(4) 1 mM EDTA; and (5) water as diluent.

More preferably, the solution formulation comprises a composition formed by mixing:

(1) about 0.2 to about 4 mg/ml of a KGF-2 polypeptide;

(2) 20 mM sodium acetate;

(3) 125 mM NaCl;

(4) 1 mM EDTA; and (5) water as a diluent, wherein the solution is at about pH 6.2 and is stored at about −20° C.

The present inventors have discovered that KGF-2 polypeptides readily oxidize, aggregate and precipitate out of solution. Although oxidation of KGF-2 does not destroy biological activity, limiting the extent of oxidation of the product leads to a more stable product. The inventors observed that if the liquid formulation is at a pH too low the KGF-2 polypeptide will lose biological activity. Additionally, as the pH of the solution approaches the pI for KGF-2, the protein will precipitate out of solution. Thus, the inventors have determined that liquid formulations should be maintained in the range of about pH 6.0 to about pH 7.0, and that a pH of about 6.2 is most optimal for stabilizing the KGF-2 polypeptide. Moreover, the inventors surprisingly determined that a citrate buffer specifically stabilizes the KGF-2 polypeptides.

Although, the use of a citrate buffer having at about pH 6.0–6.2 provides a liquid formulation that reduces aggregation of the KGF-2 polypeptide and increases stability, the liquid polypeptide formulation may still be subject to oxidation and precipitation of KGF-2 polypeptides. Thus, the inventors developed a lyophilized formulation as set forth below.

Lyophilized Formulations

A second aspect of the present invention is directed to lyophilizated formulations of KGF-2 polypeptides that comprise: a KGF-2 polypeptide and a buffer having a buffering capacity of between about pH 5.0 and about pH 8.0, more preferably pH 5.5 to pH 6.5, most preferably pH 6.2. Useful buffers include buffers derived from phosphate, aconitic, citric, glutaric, malic, succinic and carbonic acids. Typically employed is an alkali or alkaline earth salt of one of the aforementioned acids. More preferably the buffer will be phosphate or citrate, most preferably citrate. For example, the formulation may comprise a composition formed by mixing a buffering amount of citric acid or a pharmaceutically acceptable salt thereof with KGF-2 Δ33 in water. The preferable buffer concentration is from about 5 mM to about 50 mM and more preferably at about 10 mM. Most preferably, the citrate buffer will be added in a concentration of about 10 mM. Also preferably included in the formulation is NaCl as a tonicifier at a concentration of from about 0.01 mM to about 150 mM, most preferably at about 20 mM and a metal chelating agent, such as EDTA, at a concentration of from about 0.01 mM to about 10 mM, most preferably at about 1 mM. In addition, bulking agents/cryoprotectants such as sucrose, glycine, mannitol, trehalose or other pharmaceutically acceptable bulking agents are included in the formulation. The amount of bulking agent used will be such that the solution is isotonic and is in a range of about 2% to about 10% w/v. Preferred concentrations are as follows: 5% mannitol, 7% sucrose, 8% trehalose, or 2% glycine +0.5% sucrose. More preferably, sucrose or sucrose/glycine mixture is used. Additionally, a lyophilized formulation of the present invention may also include one or more of (a) a stabilizing amount of an antioxidant, such as ascorbate or (b) a stabilizing amount of thiol-compound, for example monothioglycerol. Storage conditions for the lyophilized formulation are typically at about 2° C. to about 25° C. More preferably storage conditions are at or below about 2° C. to about 8° C.

KGF-2 polypeptides are lyophilized at a concentration of about 0.02 mg/ml to about 10 mg/ml of protein in the initial solution The initial lyophilization solution preferably comprises (in addition to the KGF-2 polypeptides):

(1) an effective amount of citric acid or a pharmaceutically acceptable salt thereof, preferably sodium citrate, at a concentration range of about 5 mM to about 20 mM;

(2) NaCl at a concentration range of about 0.01 mM to about 125 mM, (3) EDTA at a concentration range of about 0.1 mM to about 10 mM (4) one or more of sucrose, mannitol, glycine or trehalose at a concentration range of about 2% w/v to about 15% w/v; and (5) water.

The preferred pH range for the lyophilization buffer is from about 5.5 to about 8.0, preferably about pH 6.2.

More preferably, the lyophilization buffer comprises 10 mM sodium citrate, 20 mM sodium chloride, 1 mM disodium EDTA at pH 6.2 and 7% sucrose.

The lyophilized KGF-2 polypeptide formulations are reconstituted in sterile water so as to maintain isotonic conditions of about 290 mOsm. The KGF-2 polypeptides can be reconstituted in sterile water, optionally containing a stabilizing amount of antioxidants comprising: a) about 0.01% to about 2% w/v monothioglycerol, b) about 0.01% to about 2% w/v ascorbic acid, c) about 0.01% to about 2% w/v methionine or d) combinations thereof.

The present invention includes lyophilization cycles that yield a stable KGF-2 polypeptide formulation. The lyophilization cycle is designed to keep the KGF-2 polypeptide product below its collapse temperature during the primary drying phase. Additionally, the moisture content is targeted to be preferably less than 5%, and more preferably less than 2%. Such a protocol must be determined for any particular protein on an individual basis. An example lyophilization cycle for the KGF-2 sucrose containing lyophilization formulation according to the present invention was determined to be as follows:

| Temperature (° C.) | Pressure (mTorr) | Time (min.) |
| --- | --- | --- |
| 5 (hold) | atmospheric | 60 |
| 5 to −45 (ramp) | atmospheric | 120 |
| −45 (hold) | atmospheric | 120 |
| −45 (hold) | 75 to 100 | 60 |
| −45 to −20 (ramp) | 75 to 100 | 125 |
| −20 (hold) | 75 to 100 | 2100 |
| −20 to +25 (ramp) | 75 to 100 | 225 |
| +25 (hold) | 75 to 100 | 1020 |

The lyophilization formulation of the present invention provides a product with unexpectedly increased stability. Indeed, lyophilized KGF-2 formulations of the present invention are biologically stable for at least 9 months at temperatures of up to 45° C. (FIG. 4). Reverse-phase HPLC demonstrated that the lyophilized KGF-2 formulations of the present invention retained its physio-chemical properties for up to 8 months at temperatures of at or below 45° C. and 75% relative humidity. Stability for this length of time at such high temperatures is very unusual for proteins.

Thickened and Gel Formulations

A third aspect of the invention is directed to thickened or gel formulations for KGF-2 polypeptides.

1) Thickening Agents:

Thickening agents may be added to the above described liquid formulations to increase the viscosity of the resulting formulation. A formulation having an increased viscosity may be beneficial for topical applications where controlled release, adhering to the shape of a wound or avoiding run-off may be important. Such thickened formulations are employed for topical uses such as wound healing, to treat skin disorders or any other use which could be treated via topical application of a KGF-2 pharmaceutical composition.

The thickening agent should raise the viscosity to about 50 to about 10,000 cps (centipoise), more preferably about 50 to about 1,000 cps (centipoise) and most preferably about 200 to about 300 cps (centipoise). Viscosity is measured using a rotating spindle viscometer. The most preferred concentration of thickening agent is 0 to 5% (w/w). The thickened solution will stay liquid at all times.

Examples of appropriate thickening agents include, but are not limited to water soluble etherified celluloses and carbomer (high molecular weight polymers of acrylic acid cross-linked with either allylsucrose or allyl ethers of pentaerythritol). Examples of etherified cellulose are well known in the art (listed in USP) and include alkyl celluloses, hydroxyalkyl celluloses and alkylhydroxyalkyl celluloses e.g., methylcellulose, hydroxyethyl cellulose, hydroxy propyl cellulose, hydroxy propyl methylcellulose, and the like. In a further embodiment, the topical or incisional gel may comprise about 0 to about 20% by weight of a cellulose derivative having a molecular weight of about 50,000 to about 700,000. In a preferred embodiment the cellulose derivative is present at about 2% to about 8% by weight and has a molecular weight in the range of about 80,000 to about 240,000. Preferred cellulose derivatives are hydroxypropylmethyl cellulose, methyl cellulose, carboxymethyl cellulose, and hydroxyethyl cellulose.

When thickening agents are added to the injectable formulations, detailed above, salts and buffering agents may be added or removed from the formulation for optimal stability. For example, the citrate concentration may be increased. Preferred concentrations for citrate are for example, about 10 mM to about 500 mM citrate, more preferably about 10 mM to about 50 mM citrate and most preferably about 10 mM to about 20 mM citrate. Additionally, the amount of sucrose may be decreased in the lyophilization formulation to a range from about 0% to about 5% sucrose.

Thickening agents may be added directly to a liquid formulation according to the present invention and then lyophilized. Alternatively, a lyophilized formulation according to the present invention may be reconstituted by adding a suitable diluent, most preferably water having a thickening agent dissolved therein.

Such thickened formulations could be administered by spray.

An example of a preferred thickened KGF-2 polypeptide solution according to the present invention comprises a product formed by mixing:

(1) a topically effective amount of a KGF polypeptide, preferably KGF-2 Δ33;

(2) about 10 mM to about 500 mM sodium citrate buffer;

(3) about 0.01 to about 150 mM NaCl;

(4) about 0.75 to about 1.27 mM, preferably about 1 mM EDTA;

(5) about 0.1% to about 7% sucrose;

(6) about 0.75 to about 1.5% (w/w) carboxy methyl cellulose or about 0.5 to about 1.5% hydroxy propyl methyl cellulose or about 0.25 to about 0.75% hydroxy ethyl cellulose or about 0 to 1% carbomer or any combination thereof.

The a pH of such a formulation is most preferably pH 6.2.

2) Gelling Agents:

Another aspect of the present invention is directed to gel formulations for KGF-2 polypeptides. Gelling agents may be added to injectable formulations of the present invention to provide a formulation that remains liquid at room temperature and solidifies when applied to the surface of the skin (at about 37° C.). Such formulations may be useful for topical applications where controlled release, adhering to the shape of a wound or avoiding run-off may be important. Such gel formulations are employed for topical uses such as wound healing, to treat skin disorders or any other use which could be treated via topical application of KGF-2 pharmaceutical composition.

Gel formulations for KGF-2 polypeptides according to the present invention comprise:

(1) a topically effective amount of a KGF polypeptide;
(2) a buffer;
(3) a pharmaceutically acceptable diluent, preferably water; and
(4) a gel-forming high molecular weight compound.

Viscosity of gel formulations of the present invention may be in a range of about 1 to about 10,000 cps at room temperature, most preferred about 20 to about 100 cps at room temperature. Viscosity is measured using a rotating spindle viscometer.

Gel forming high molecular weight compounds employed in the present invention are typically water-soluble polymers capable of forming a viscous aqueous solution, or non-water soluble, water-swellable polymers (e.g., collagen) that can also form a viscous solution and that gel upon contact with skin.

Useful gel forming high molecular weight compounds may be selected from vinyl polymers, polyoxyethylene-polyoxypropylene copolymers, polysaccharides, proteins, poly(ethylene oxide), acrylamide polymers and derivatives and or salts thereof Other compounds that can be used to make pharmaceutical gel formulations used in healing wounds can be found in U.S. Pat. No. 5,427,778, which is herein fully incorporated by reference.

Useful vinyl polymers (or substituted polyethylenes) include polyacrylic acid, polymethacrylic acid, polyvinyl pyrrolidone and polyvinyl alcohol. Useful polysaccharides include cellulose derivatives, glycosaminoglycans, agar, pectin, alginic acid, dextran, starch (α-amylose or amylopectin), and chitosan. Useful glycosaminoglycans include hyaluronic acid, chondroitin, chondroitin-4-sulfate, heparan sulfate and heparin. The glycosaminoglycans may be used to enhance wound healing in combination with any other gel forming polymer such as, for example, collagen, gelatin, fibronectin. The acrylamide polymers may be polyacrylamide or polymethacrylamide polymers.

Preferred high molecular weight gel forming compounds are polyoxyethylene-polyoxypropylene block copolymers, especially those block copolymers that are designated in the trade as PLURONICS (BASF) or POLAXAMERS (BASF).

In one preferred embodiment, the gel of the present invention may comprise about 10 to about 60% by weight of a polyoxyethylene-polyoxypropylene block copolymer having an average molecular weight of about 500 to 50,000. In a more preferred embodiment, the gel of the present invention may comprise about 14 to about 18% by weight of block copolymers having a molecular weight in the range 1,000 to 15,000. Preferred block copolymers of the present invention are Pluronic F108 (BASF, average molecular weight: 14,600) and Pluronic F127 (BASF, average molecular weight: 12,600).

Polyoxyethylene-polyoxpropylene block copolymers (Pluronic or Poloxamer) have great potential for use in topical drug delivery systems because they exhibit reverse thermal gelation behavior, have good drug release characteristics as well as low toxicity. Gels are formed as the solution is warmed. Thus, the gel is a low viscosity aqueous solution at room temperature but when it contacts the mammalian body and is warmed by body temperature the viscosity increases as the solution gels. Pluronic gels can be used for the controlled delivery of KGF-2 polypeptides to, for example, wounds and other such sites where topical delivery is desirable. KGF-2 polypeptides can be combined with the Pluronic in the liquid state and applied to the wound. Gelation occurs and effectively reduces the rate that the polypeptides are released to the wound and thereby permits prolonged contact between the polypeptides and the wound site. The benefits of using such gel formulations include keeping the wound moist and having a pharmaceutical compound that is form-fitting to the wound or other such site where the compound may be applied.

The preferred gel formulations for KGF-2 polypeptides according to the present invention comprises citrate buffer and a Pluronic. The formulation may comprise an amount of citric acid or a pharmaceutically acceptable salt, thereof.

The gel formulation according to the present invention may also include an chelating agent, a stabilizing amount of antioxidants or thiols. The gel formulation will include a high molecular weight compound, such as a Pluronic, or water-soluble etherified cellulose, and the like in an amount that will form a gel. In the gel formulation according to the present invention, the KGF-2 polypeptides are preferably in a concentration of about 0.01 mg/ml to about 10 mg/ml. Preferably, the gel formulations are formed by mixing:

(1) a KGF-2 polypeptide, preferably KGF-2 Δ33, in a final calculated concentration of 0.01 mg/ml to about 10 mg/ml;
(2) an effective amount of a buffering agent;
(3) about 10% to about 60%, or more preferably about 14% to about 18% by weight of a polyoxyethylene-polyoxypropylene block copolymer having an average molecular weight of about 500 to 50,000; and
(4) a pharmaceutically acceptable diluent, preferably water Another preferred gel formulation comprises:
(1) a pharmaceutically active amount of KGF-2 polypeptide;
(2) about 10 mM to about 500 mM sodium citrate;
(3) about 0.01 mM to about 150 mM NaCl;
(4) about 1 mM EDTA,
(5) about 0.1% to about 7% sucrose;
(6) about 14% to about 18% Pluronic F127; and
(7) water,
wherein the formulation is at a pH of about pH 6.2.

Most preferably, the gel formulation comprises:
(1) a KGF-2 polypeptide, preferably KGF-2 Δ33, at a concentration range of about 0.01 mg/ml to about 10 mg/ml (w/v), more preferably about 0.1 mg/ml to about 3 mg/ml, and most preferably about 0.2 mg/ml;
(2) sodium citrate at a concentration range of about 5 mM to about 20 mM;
(3) about 10% to about 25% (w/v), preferably about 15 to about 25, and most preferably about 16% of Pluronic 127 or Poloxamer 407;
(4) about 6.7% to about 7.3% sucrose, preferably about 7% sucrose; and
(5) water to volume.

The gel formulation optionally further includes one or more of the following:
(6) EDTA at a concentration range of about 0.1 mM to about 1 0 mM.
(7) NaCl at a concentration range of about 0.01 mM to about 125 mM. The preferred pH ranges for the gel formulation is from about pH 5.0 to about pH 8.0, preferably pH 6.2 and the resulting gel formulation should be isotonic.

3) Additional Stabilizing Agents:

All of the foregoing formulations of the present invention may benefit from from anti-oxidants, metal chelating agents, thiol containing compounds and other general stabilizing agents. Examples of such stabilizing agents, include, but are not limited to:

(a) about 0.5% to about 2% w/v glycerol,
(b) about 0.1% to about 1% w/v methionine,
(c) about 0.1% to about 2% w/v monothioglycerol,
(d) about 1 mM to about 10 mM EDTA,
(e) about 0.01% to about 2% w/v ascorbic acid,
(f) 0.003% to about 0.02% w/v polysorbate 80,
(g) 0.001% to about 0.05% w/v polysorbate 20,
(h) arginine,
(i) heparin,
(j) dextran sulfate,
(k) cyclodextrins, or
(l) combinations thereof Administration of KGF-2 Polypeptides The KGF-2 polypeptide formulations of the present invention may employ suitable pharmaceutical diluents that are known to be useful in pharmaceutical compositions. Such a diluents include but are not limited to, saline, buffered saline, dextrose, water, glycerol, ethanol, and combinations thereof The formulation should suit the mode of administration. Preferably, the pharmaceutical compositions will be formulated according to the present invention, as indicated above. Water is a preferred diluent.

The polypeptide having KGF-2 activity may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition, including whether another agent, if any, is employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in *Remington's Pharmaceutical Sciences* (latest edition), Mack Publishing Company, Easton, Pa. The "effective amount" of KGF-2 for purposes herein (including a KGF-2 effective amount) is thus determined by such considerations.

The pharmaceutical compositions of the present invention may be administered in a convenient manner such as by the oral, rectal, topical, intravenous, intraperitoneal, intramuscular, intraarticular, subcutaneous, intranasal, inhalation, intraocular or intradermal routes. Parenteral and topical delivery are the preferred routes of administration. The term "parenteral" as used herein refers to modes of administration which include intravenous, intramuscular, intraperitoneal, intrasternal, subcutaneous and intraarticular injection and infusion.

The pharmaceutical compositions are administered in an amount which is effective for treating and/or prophylaxis of the specific indication. In most cases, the KGF-2 dosage is from about 1 µg/kg to about 30 mg/kg body weight daily, taking into account the routes of administration, symptoms, etc. However, the dosage can be as low as 0.001 µg/kg. For example, in the specific case of topical administration dosages are preferably administered from about 0.01 µg to 9 mg per cm$^2$. In the case of intranasal and intraocular administration, dosages are preferably administered from about 0.001 µg/ml to about 10 mg/ml, and more preferably from about 0.05 mg/ml to about 4 mg/ml.

As a general proposition, the total pharmaceutically effective amount of the KGF-2 polypeptide administered parenterally will be in the range of about 1 µg/kg/day to 10 mg/kg/day of patient body weight, although, as noted above, this will be subject to therapeutic discretion. If given continuously, the KGF-2 polypeptide is typically administered at a dose rate of about 1 µg/kg/hour to about 50 µg/kg/hour, either by 1–4 injections per day or by continuous subcutaneous infusions, for example, using a mini-pump. An intravenous bag solution or bottle solution may also be employed.

A course of KGF-2 polypeptide treatment to affect the fibrinolytic system appears to be optimal if continued longer than a certain minimum number of days, 7 days in the case of the mice. The length of treatment needed to observe changes and the interval following treatment for responses to occur appears to vary depending on the desired effect.

For parenteral administration, in one embodiment, the KGF-2 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the KGF-2 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in *Remington's Pharmaceutical Sciences* (latest edition), Mack Publishing Company, Easton, Pa.

KGF-2 polypeptides may also be administered to the eye to treat lacrimal gland injuries, disorders and pathologies in animals and humans as a liquid, drop, or thickend liquid, a gel.

KGF-2 polypeptides can also be intranasally administered to the nasal mucosa to treat disorders, injuries and pathologies of the nasal mucosa and sinus epithelia in animals and humans as liquid drops or in a spray form.

Generally, the formulations are prepared by contacting the KGF-2 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in *Remington's Pharmaceutical Sciences* (latest edition), Mack Publishing Company, Easton, Pa.

The carrier may also contain minor amounts of suitable additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG KGF-2 is typically formulated in such vehicles at a concentration of about 0.01 µg/ml to 50 mg/ml, preferably 0.01 µg/ml to 10 mg/ml, at a pH of about 5 to about 8, preferably about 6 to about 7, most preferably about pH 6.2. It will be understood that the use of certain of the foregoing excipients, carriers, or stabilizers will result in the formation of KGF-2 salts.

KGF-2 to be used for therapeutic administration may be sterile. Sterility is readily accomplished by filtration through sterile filtration membranes (e.g., 0.2 micron membranes). Therapeutic KGF-2 compositions may be placed into a container having a sterile access port, for example, an intravenous solution bag or vial having a stopper pierceable by a hypodermic injection needle.

KGF-2 ordinarily will be stored in unit or multi-dose containers, for example, sealed ampules or vials, as an aqueous solution or as a lyophilized formulation for reconstitution. As an example of a lyophilized formulation, 3-ml vials are filled with 1 ml of sterile-filtered 1% (w/v) aqueous KGF-2 solution, and the resulting mixture is lyophilized. The infusion solution is prepared by reconstituting the lyophilized KGF-2 using Water-for-Injection which may optionally include one or more antioxidants.

Dosaging may also be arranged in a patient specific manner to provide a predetermined concentration of an KGF-2 activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

The KGF-2 is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (U. Sidman et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Sustained-release KGF-2 compositions also include liposomally entrapped KGF-2. Liposomes containing KGF-2 are prepared by methods known per se: DE 3,218,121; Epstein, et al., *Proc. Natl. Acad Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal KGF-2 therapy.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

When the present inventors examined the biological activity and stability of the KGF-2 polypeptide prepared according to the formulations of the present invention, it was surprisingly discovered that the use of monothioglycerol may stabilize the KGF-2 polypeptides and may behave as a potentiating agent for KGF-2 polypeptides in wound healing. The optimal concentration range for the potentiating effect of the monothioglycerol was 0.1% to 2% w/v.

KGF-2 Polypeptides

KGF-2 stimulates the proliferation of epithelial cells and epidermal keratinocyes but not mesenchymal cells such as fibroblasts. Thus, "a polypeptide having KGF-2 protein-like activity" includes polypeptides that exhibit the KGF-2 activity, in the keratinocyte proliferation assay set forth below and U.S. application Ser. No. 08/910,875 and can bind to the FGF receptor isoforms 1-iiib and 2-iiib. Although the degree of activity need not be identical to that of the KGF-2 protein, preferably, "a polypeptide having KGF-2 protein-like activity" exhibits substantially similar activity as compared to the KGF-2 protein (i.e., the candidate polypeptide exhibits greater activity or not more than tenfold less and, preferably, not more than about twofold less activity relative to the reference KGF-2 protein).

The KGF-2 polypeptides used in the formulations of the present invention may or may not have the N-terminal methionine, preferably the polypeptide will be lacking the N-terminal methionine.

The KGF-2 cDNA clone was deposited as ATCC Deposit No. 75977 on Dec. 16, 1994 at the American Type Culture Collection, Patent Depository, 10801 University Blvd, Manassas, Va. 20110-2209. In addition, a cDNA encoding KGF-2 Δ33 inserted into an expression vector, pHE4-5, was deposited at the ATCC on Jan. 9, 1998 as ATCC No. 209575.

The terms "fragment," "derivative" and "analog" when referring to the polypeptide, of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the KGF-2 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

The polypeptides of the present invention are preferably in an isolated form. By "isolated polypeptide" is intended a polypeptide removed from its native environment. Thus, a polypeptide produced and/or contained within a recombinant host cell is considered isolated for purposes of the present invention. Also intended are polypeptides that have been purified, partially or substantially, from a recombinant host cell or a native source.

The pharmaceutical formulations of the present invention include the KGF-2 polypeptide of SEQ ID NO:2 (in particular the mature polypeptide) and deletion mutants thereof, as well as polypeptides which have at least 90%, 95%, 96%, 97%, 98%, 99% similarity (more preferably at least 90%, 95%, 96%, 97%, 98%, 99% identity) to the polypeptide of SEQ ID NO:2 and deletion mutants thereof, and also include portions of such polypeptides with such portion of the polypeptide (such as the deletion mutants described below) generally containing at least 30 amino acids and more preferably at least 50 amino acids.

As known in the art "similarity" between two polypeptides is determined by comparing the amino acid sequence and its conservative amino acid substituted sequence of one polypeptide to the sequence of a second polypeptide.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482–489, 1981) to find the best segment of similarity between two sequences.

By a polypeptide having an amino acid sequence at least, for example, 95% "identical" to a reference amino acid sequence of a KGF-2 polypeptide is intended that the amino acid sequence of the polypeptide is identical to the reference sequence except that the polypeptide sequence may include up to five amino acid alterations per each 100 amino acids of the reference amino acid of the KGF-2 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 [SEQ ID NO:2] or to the amino acid sequence encoded by deposited cDNA clone can be determined conventionally using known computer programs such the Bestfit program (Wisconsin Sequence Analysis Package, Version 8 for Unix, Genetics Computer Group, University Research Park 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

KGF-2 Deletion Mutants

Native KGF-2 is relatively unstable in the aqueous state and it undergoes chemical and physical degradation resulting in loss of biological activity during processing and storage. Native KGF-2 is also prone to aggregation in aqueous solution, at elevated temperatures and it becomes inactivated under acidic conditions.

Particularly preferred KGF-2 polypeptides are the deletion mutants shown below (numbering starts with the first amino acid in the protein (Met):

Thr (residue 36)—Ser (residue 208) Ser (46)—Ser (208)
Cys (37)—Ser (208) Pro (47)—Ser (208)
Gln (38)—Ser (208) Glu (48)—Ser (208)
Ala (39)—Ser (208) Ala (49)—(Ser (208)
Leu (40)—Ser (208) Thr (50)—Ser (208)
Gly (41)—Ser (208) Asn (51)—Ser (208)
Gln (42)—Ser (208) Ser (52)—Ser (208)
Asp (43)—Ser (208) Ser (53)—Ser (208)
Met (44)—Ser (208) Ser (54)—Ser (208)
Val (45)—Ser (208) Ser (55)—Ser (208)
Ser (56)—Ser (208)
Phe (57)—Ser (208)
Ser (59)—Ser (208)
Ser(62)—Ser (208)
Ala(63)—Ser (208)
Gly (64)—Ser (208)
Arg (65)—Ser (208)
Val (67)—Ser (208)
Ser (69)—Ser (208)
Val (77)—Ser (208)
Arg (80)—Ser (208)
Met(1), Thr (36), or Cys (37)—His (207)
Met (1), Thr (36), or Cys (37)—Val (206)
Met (1), Thr (36), or Cys (37)—Val (205)
Met(1), Thr (36), or Cys (37)—Met (204)
Met(1), Thr (36), or Cys (37)—Pro (203)
Met(1), Thr (36), or Cys(37)—Leu (202)
Met(1), Thr (36), or Cys (37)—Phe (201)
Met(1), Thr (36), or Cys (37)—His (200)

Met(1), Thr (36), or Cys (37)—Ala (199)
Met (1), Thr (3 6), or Cys (37)—Ser (198)
Met (1), Thr (3 6), or Cys (37)—Thr (197)
Met(1), Thr (36), or Cys (37)—Asn (196)
Met(1), Thr (36), or Cys (37)—Lys (195)
Met(1), Thr (36), or Cys (37)—Arg (194)
Met(1), Thr (36), or Cys (37)—Arg (193)
Met(1), Thr (36), or Cys (37)—Thr (192)
Met(1), Thr (36), or Cys (37)—Lys (191)
Met(1), Thr (36), or Cys (37)—Arg (188)
Met(1), Thr (36), or Cys (37)—Arg (187)
Met(1), Thr (36), or Cys (37)—Lys (183)

Preferred embodiments include the N-terminal deletions Ala (63)—Ser (208) (KGF-2Δ28) and Ser (69)—Ser (208) (KGF-2Δ33). Other preferred N-terminal and C-terminal deletion mutants include: Ala (39)—Ser (208); Pro (47)—Ser (208); Val (77)—Ser (208); Glu (93)—Ser (208); Glu (104)—Ser (208); Val (123)—Ser (208); and Gly (138)—Ser (208). Other preferred C-terminal deletion mutants include: Met (1), Thr (36), or Cys (37)—Lys (153).

Also included by the present invention are deletion mutants having amino acids deleted from both the N-terminus and the C-terminus. Such mutants include all combinations of the N-terminal deletion mutants and C-terminal deletion mutants described above, e.g., Ala (39)—His (200), Met (44)—Arg (193), Ala (63)—Lys (153), Ser (69)—Lys (153), etc. Those combinations can be made using recombinant techniques known to those skilled in the art.

Thus, preferred KGF polypeptides for use in pharmaceutical formulations of the present invention comprise N-terminal deletion mutants, including those comprising the amino acid sequence shown in FIG. 1 (SEQ ID NO:2) except for a deletion of at least the first 38 N-terminal amino acid residues (i.e., a deletion of at least Met (1)—Gln (38)) but not more than the first 147 N-terminal amino acid residues of FIG. 1 (SEQ ID NO:2). Alternatively, the formulation comprises a mutant having a deletion that will include at least the first 38 N-terminal amino acid residues (i.e., a deletion of at least Met (1)—Gln (38)) but not more than the first 137 N-terminal amino acid residues of FIG. 1 (SEQ ID NO:2). Alternatively, the formulation comprises a mutant having a deletion that will include at least the first 46 N-terminal amino acid residues but not more than the first 137 N-terminal amino acid residues of FIG. 1 (SEQ ID NO:2). Alternatively, the formulation comprises a mutant having a deletion that will include at least the first 62 N-terminal amino acid residues but not more than the first 137 N-terminal amino acid residues of FIG. 1 (SEQ ID NO:2). Alternatively, the formulation comprises a mutant having a deletion that will include at least the first 68 N-terminal amino acid residues but not more than the first 137 N-terminal amino acid residues of FIG. 1 (SEQ ID NO:2). Alternatively, the formulation comprises a mutant having a deletion that will include at least the first 76 N-terminal amino acid residues but not more than the first 137 N-terminal amino acid residues of FIG. 1 (SEQ ID NO:2). Alternatively, the formulation comprises a mutant having a deletion that will include at least the first 92 N-terminal amino acid residues but not more than the first 137 N-terminal amino acid residues of FIG. 1 (SEQ ID NO:2). Alternatively, the formulation comprises a mutant having a deletion that will include at least the first 103 N-terminal amino acid residues but not more than the first 137 N-terminal amino acid residues of FIG. 1 (SEQ ID NO:2). Alternatively, the formulation comprises a mutant having a deletion that will include at least the first 122 N-terminal amino acid residues but not more than the first 137 N-terminal amino acid residues of FIG. 1 (SEQ ID NO:2).

In addition to a formulation comprising a KGF-2 mutant with the ranges of N-terminal deletion mutants described above, the present invention is also directed to a formulation having all combinations of the above described ranges, e.g., deletions of at least the first 62 N-terminal amino acid residues but not more than the first 68 N-terminal amino acid residues of FIG. 1 (SEQ ID NO:2); deletions of at least the first 62 N-terminal amino acid residues but not more than the first 76 N-terminal amino acid residues of FIG. 1 (SEQ ID NO:2); deletions of at least the first 62 N-terminal amino acid residues but not more than the first 92 N-terminal amino acid residues of FIG. 1 (SEQ ID NO:2); deletions of at least the first 62 N-terminal amino acid residues but not more than the first 103 N-terminal amino acid residues of FIG. I (SEQ ID NO:2); deletions of at least the first 68 N-terminal amino acid residues but not more than the first 76 N-terminal amino acid residues of FIG. 1 (SEQ ID NO:2); deletions of at least the first 68 N-terminal amino acid residues but not more than the first 92 N-terminal amino acid residues of FIG. 1 (SEQ ID NO:2); deletions of at least the first 68 N-terminal amino acid residues but not more than the first 103 N-terminal amino acid residues of FIG. 1 (SEQ ID NO:2); deletions of at least the first 46 N-terminal amino acid residues but not more than the first 62 N-terminal amino acid residues of FIG. 1 (SEQ ID NO:2); deletions of at least the first 46 N-terminal amino acid residues but not more than the first 68 N-terminal amino acid residues of FIG. 1 (SEQ ID NO:2); deletions of at least the first 46 N-terminal amino acid residues but not more than the first 76 N-terminal amino acid residues of FIG. 1 (SEQ ID NO:2); etc.

In another embodiment, formulations comprising C-terminal deletion mutants are provided by the present invention. Preferably, the N-terminal amino acid residue of said C-terminal deletion mutants is amino acid residue 1 (Met), 36 (Thr), or 37 (Cys) of FIG. 1 (SEQ ID NO:2). Such formulations comprising mutants include those comprising the amino acid sequence shown in FIG. 1 (SEQ ID NO:2) except for a deletion of at least the last C-terminal amino acid residue (Ser (208)) but not more than the last 55 C-terminal amino acid residues (i.e., a deletion of amino acid residues Glu (154)—Ser (208)) of FIG. 1 (SEQ ID NO:2). Alternatively, the formulation comprises a mutant having a deletion that will include at least the last C-terminal amino acid residue but not more than the last 65 C-terminal amino acid residues of FIG. 1 (SEQ ID NO:2). Alternatively, the formulation comprises a mutant having a deletion that will include at least the last 10 C-terminal amino acid residues but not more than the last 55 C-terminal amino acid residues of FIG. 1 (SEQ ID NO:2). Alternatively, the formulation comprises a mutant having a deletion that will include at least the last 20 C-terminal amino acid residues but not more than the last 55 C-terminal amino acid residues of FIG. 1 (SEQ ID NO:2). Alternatively, the formulation comprises a mutant having a deletion that will include at least the last 30 C-terminal amino acid residues but not more than the last 55 C-terminal amino acid residues of FIG. 1 (SEQ ID NO:2). Alternatively, the formulation comprises a mutant having a deletion that will include at least the last 40 C-terminal amino acid residues but not more than the last 55 C-terminal amino acid residues of FIG. 1 (SEQ ID NO:2). Alternatively, the formulation comprises a mutant having a deletion that will include at least the last 50 C-terminal amino acid residues but not more than the last 55 C-terminal amino acid residues of FIG. 1 (SEQ ID NO:2).

In addition to a formulation comprising a KGF-2 mutant with the ranges of C-terminal deletion mutants described above, the present invention is also directed to a formulation having all combinations of the above described ranges, e.g., deletions of at least the last C-terminal amino acid residue but not more than the last 10 C-terminal amino acid residues of FIG. 1 (SEQ ID NO:2); deletions of at least the last C-terminal amino acid residue but not more than the last 20 C-terminal amino acid residues of FIG. 1 (SEQ ID NO:2); deletions of at least the last C-terminal amino acid residue but not more than the last 30 C-terminal amino acid residues of FIG. 1 (SEQ ID NO:2); deletions of at least the last C-terminal amino acid residue but not more than the last 40 C-terminal amino acid residues of FIG. 1 (SEQ ID NO:2); deletions of at least the last 10 C-terminal amino acid residues but not more than the last 20 C-terminal amino acid residues of FIG. 1 (SEQ ID NO:2); deletions of at least the last 10 C-terminal amino acid residues but not more than the last 30 C-terminal amino acid residues of FIG. 1 (SEQ ID NO:2); deletions of at least the last 10 C-terminal amino acid residues but not more than the last 40 C-terminal amino acid residues of FIG. 1 (SEQ ID NO:2); deletions of at least the last 20 C-terminal amino acid residues but not more than the last 30 C-terminal amino acid residues of FIG. 1 (SEQ ID NO:2); etc.

In yet another embodiment, the KGF-2 polypeptide can be a deletion mutant having amino acids deleted from both the N- terminal and C-terminal residues. Such mutants include all combinations of the N-terminal deletion mutants and C-terminal deletion mutants described above. Such mutants include those comprising the amino acid sequence shown in FIG. 1 (SEQ ID NO:2) except for a deletion of at least the first 46 N-terminal amino acid residues but not more than the first 137 N-terminal amino acid residues of FIG. 1 (SEQ ID NO:2) and a deletion of at least the last C-terminal amino acid residue but not more than the last 55 C-terminal amino acid residues of FIG. 1 (SEQ ID NO:2). Alternatively, a deletion can include at least the first 62, 68, 76, 92, 103, or 122 N-terminal amino acids but not more than the first 137 N-terminal amino acid residues of FIG. 1 (SEQ ID NO:2) and a deletion of at least the last 10, 20, 30, 40, or 50 C-terminal amino acid residues but not more than the last 55 C-terminal amino acid residues of FIG. 1. Further included are all combinations of the above described ranges.

KGF-2 Substitution Mutants

Useful KGF-2 polypeptides include those having substitution of amino acids. Native mature KGF-2 contains 44 charged residues, 32 of which carry a positive charge. Depending on the location of such residues in the protein's three dimensional structure, substitution of one or more of these clustered residues with amino acids carrying a negative charge or a neutral charge may alter the electrostatic interactions of adjacent residues and may be useful to achieve increased stability and reduced aggregation of the protein. Aggregation of proteins cannot only result in a loss of activity but be problematic when preparing pharmaceutical formulations, because they can be immunogenic (Pinckard et al, Clin. Exp. Immunol. 2:331–340 (1967), Robbins et al, Diabetes 36:838–845 (1987), Cleland et al., Crit. Rev. Therapeutic Drug Carrier Systems 10:307–377 (1993)). Any modification should give consideration to minimizing charge repulsion in the tertiary structure of the protein molecule. Thus, of special interest are substitutions of charged amino acid with another charge and with neutral or negatively charged amino acids. The latter results in proteins with a reduced positive charge to improve the characteristics of KGF-2. Such improvements include increased stability and reduced aggregation of the analog as compared to the native KGF-2 protein.

The replacement of amino acids can also change the selectivity of binding to cell surface receptors. Ostade et al., Nature 361:266–268 (1993), described certain TNF alpha mutations resulting in selective binding of TNF alpha to only one of the two known TNF receptors.

KGF-2 molecules may include one or more amino acid substitutions, deletions or additions, either from natural mutation or human manipulation. Examples of some preferred mutations are: Ala (49) Gln, Asn (51) Ala, Ser (54) Val, Ala (63) Pro, Gly (64) Glu, Val (67) Thr, Trp (79) Val, Arg (80) Lys, Lys (87) Arg, Tyr (88) Trp, Phe (89) Tyr, Lys (91) Arg, Ser (99) Lys, Lys (102) Gln, Lys 103(Glu), Glu (104) Met, Asn (105) Lys, Pro (107) Asn, Ser (109) Asn, Leu (111) Met, Thr (114) Arg, Glu(117) Ala, Val (120) Ile, Val (123) Ile, Ala (125) Gly, Ile (126) Val, Asn (127) Glu, Asn (127) Gln, Tyr (130) Phe, Met (134) Thr, Lys (136) Glu, Lys (137) Glu, Gly (142) Ala, Ser (143) Lys, Phe (146) Ser, Asn (148) Glu, Lys (151) Asn, Leu (152) Phe, Glu (154) Gly, Glu (154) Asp, Arg (155) Leu, Glu (157) Leu, Gly (160) His, Phe (167) Ala, Asn (168) Lys, Gln (170) Thr, Arg (174) Gly, Tyr (177) Phe, Gly (182) Gin, Ala (185) Val, Ala (185) Leu, Ala (185) Ile, Arg (187) Gln (190) Lys, Lys (195) Glu, Thr (197) Lys, Ser (198) Thr, Arg (1 94)Glu, Arg(194)Gln, Lys(191) Glu, Lys(191)Gln, Arg(188)Glu, Arg(188)Gln, Lys(183) Glu.

By the designation, for example, Ala (49) Gln is intended that the Ala at position 49 of FIG. 1 (SEQ ID NO:2) is replaced by Gln.

Changes are preferably of minor nature, such as conservative amino acid substitutions that do not significantly affect the folding or activity of the protein. Examples of conservative amino acid substitutions known to those skilled in the art are set forth below:

| | |
|---|---|
| Aromatic: | phenylalanine |
| | tryptophan |
| | tyrosine |
| Hydrophobic: | leucine |
| | isoleucine |
| | valine |
| Polar: | glutamine |
| | asparagine |
| Basic: | arginine |
| | lysine |
| | histidine |
| Acidic: | aspartic acid |
| | glutamic acid |
| Small: | alanine |
| | serine |
| | threonine |
| | methionine |
| | glycine |

Of course, the number of amino acid substitutions a skilled artisan would make depends on many factors, including those described above. Generally speaking, the number of substitutions for any given KGF-2 polypeptide will not be more than 50, 40, 30, 20, 10, 5, or 3, depending on the objective. For example, a number of substitutions that can be made in the C-terminus of KGF-2 to improve stability.

Amino acids in KGF-2 that are essential for function can be identified by methods well known in the art, such as site-directed mutagenesis or alanine-scanning mutagenesis (Cunningham and Wells, Science 244:1081–1085 (1989). The latter procedure introduces single alanine mutations at every residue in the molecule. The resulting mutant molecules are then tested for biological activity such as receptor binding or in vitro and in vivo proliferative activity. (See, e.g., Example 1). Sites that are critical for ligand-receptor binding can also be determined by structural analyzis such as crystalization, nuclear magnetic resonance or photoaffinity labelling. (See for example: Smith et al., *J. Mol. Biol.*, 224:899–904 (1992); and de Vos et al. *Science,* 255:306–312 (1992).)

Other useful KGF polypeptides include polypeptides having substitutions of serine for cysteine at amino acid positions 37 and 106 and 150. An uneven number of cysteines means that at least one cysteine residue is available for intermolecular crosslinks or bonds that can cause the protein to adopt an undesirable tertiary structure. Novel KGF-2 proteins that have one or more cysteines replaced by serine or e.g. alanine are generally purified at a higher yield of soluble, correctly folded protein. Although not wishing to be bound by theory, it is believed that the cysteine residue at position 106 is important for function. This cysteine residue is highly conserved among all other FGF family members.

Therapeutic Uses of KGF-2 Polypeptide Compositions

The polypeptides of the present invention may stimulate keratinocyte cell growth and proliferation. Accordingly, compositions of the present invention can be employed to stimulate epithelial cell proliferation and basal keratinocytes for the purpose of wound healing, and to stimulate hair follicle production and healing of dermal wounds. These wounds may be of superficial nature or may be deep and involve damage of the dermis and the epidermis of skin.

KGF-2 is useful for treating a number of diseases and conditions. For example, KGF-2 is active in vitro and in vivo in various wound healing models.

See, U.S. application Ser. Nos. 08/910,875, filed Aug. 13, 1997 and 09/023,082 filed Feb. 13, 1998.

The individual to which KGF-2 is administered may heal wounds at a normal rate or may be healing impaired. When administered to an individual who is not healing impaired, KGF-2 is administered to accelerate the normal healing process. When administered to an individual who is healing impaired, KGF-2 is administered to facilitate the healing of wounds which would otherwise heal slowly or not at all. A number of afflictions and conditions can result in healing impairment. These afflictions and conditions include diabetes (e.g., Type II diabetes mellitus), treatment with both steroids and non-steroid pharmacological agents, and ischemic blockage or injury.

A number of growth factors have been shown to promote wound healing in healing impaired individuals. These growth factors include growth hormone-releasing factor, platelet-derived growth factor, and basic fibroblast growth factors. Thus, the present invention also encompasses the administration of KGF-2 compositions in conjunction with one or more additional growth factors or other agent which promotes wound healing.

The compositions of the present invention also promote the healing of anastomotic and other wounds caused by surgical procedures in individuals which both heal wounds at a normal rate and are healing impaired.

The compositions of the present invention may also be employed to stimulate differentiation of cells, for example muscle cells, cells which make up nervous tissue, prostate cells, and lung cells.

The compositions of the present invention are clinically useful in stimulating wound healing of wounds including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, and burns resulting from heat exposure to extreme temperatures of heat or cold, or exposure to chemicals, in normal individuals and those subject to conditions which induce abnormal wound healing such as uremia, malnutrition, vitamin deficiencies, obesity, infection, immunosuppression and complications associated with systemic treatment with steroids, radiation therapy, and antineoplastic drugs and antimetabolites. The compositions are also useful for promoting the healing of wounds associated with ischemia and ischemic injury, e.g., chronic venous leg ulcers caused by an impairment of venous circulatory system return and/or insufficiency; for promoting dermal reestablishment subsequent to dermal loss; increasing the tensile strength of epidermis and epidermal thickness; and increasing the adherence of skin grafts to a wound bed and to stimulate re-epithelialization from the wound bed.

Other therapeutic uses for the KGF-2 polypeptides include, but are not limited to, for example, to stimulate epithelial cell proliferation and basal keratinocytes for the purpose of treating burns and skin defects such as psoriasis and epidermolysis bullosa. KGF-2 can be used to increase the adherence of skin grafts to a wound bed and to stimulate re-epithelialization from the wound bed. KGF-2 can also be used to reduce the side effects of gut toxicity that result from radiation, chemotherapy treatments or viral infections. KGF-2 can be used to treat diseases and conditions of the liver, lung, kidney, breast, pancreas, stomach, small intestine, and large intestine. KGF-2 can be used to treat inflamamatory bowel diseases, diabetes, thrombocytopenia, hypofibrinogenemia, hypoalbuminemia, hypoglobulinemia, hemorrhagic cystitis, xerostomia, keratoconjunctivitis sicca. KGF-2 can be used to stimulate the epithelial cells of the salivary glands, lacrimal glands and stimulating re-epithelialization of the sinuses and the growth of nasal mucosa.

A number of other indications that can be treated by the composition of the present invention are described in U.S. application Ser. Nos. 08/910,875, and 09/023,082 and are herein incorporated by reference.

The present invention is directed to novel liquid and lyophilyzed formulations of KGF-2 and deletion mutants thereof This invention further relates to formulations of KGF-2 for therapeutic use. The formulations provide superior stability to the active KGF-2 polypeptides and in some instances, potentiate and dramatically increase the wound-healing activity of the polypeptides.

As used herein, by "individual" is intended an animal, preferably a mammal (such as apes, cows, horses, pigs, boars, sheep, rodents, goats, dogs, cats, chickens, monkeys, rabbits, ferrets, whales, and dolphins), and more preferably a human.

The KGF-2 Δ33 polypeptide used in the formulations of the present invention may or may not have the N-terminal methionine, preferably the polypeptide will be lacking the N-terminal methionine. Stability of the KGF-2 polypeptide formulations of the present invention is determined by proliferation assays, as described herein below.

Keratinocyte Proliferation Assays

Dermal keratinocytes are cells in the epidermis of the skin. The growth and spreading of keratinocytes in the skin is an important process in wound healing. A proliferation assay of keratinocyte is therefore a valuable indicator of protein activities in stimulating keratinocyte growth and consequently, wound healing.

Keratinocytes are, however, difficult to grow in vitro. Few keratinocyte cell lines exist. These cell lines have different cellular and genetic defects. In order to avoid complications of this assay by cellular defects such as loss of key growth factor receptors or dependence of key growth factors for growth, primary dermal keratinocytes are chosen for this assay. These primary keratinocytes are obtained from Clonetics, Inc. (San Diego, Calif.).

The bioactivity of KGF-2 polypeptides can be determined by a cell proliferation assay employing murine Baf3 2b cells that have been transfected with the fibroblast growth factor 2iiib receptor (FGFR2iiib). Proliferation of the cells is measured by the incorporation of [Methyl - $^3$H]-thymidine after the cells have been exposed to the protein as described below. The assay is carried out in a 96 well tissue culture cluster plate with about 22,000 Baf3 2b cells in each well. The cells are exposed to different concentrations of a KGF-2 polypeptide in triplicate and incubated at 37° C. in a $CO_2$ incubator for approximately 48 hours. An approximate amount of cell media containing labelled thymidine is subsequently added into each well and the incubation is continued for another 5 hours. The cells are then harvested on a glass fiber filter mat, in the 96 well format, using a cell harvester. The filter mats are dried and radioactivity incorporated into each sample is counted using a flat-bed liquid scintillation counter. Under these assay conditions, cells exposed to KGF-2 show an increased incorporation of radioactivity compared to control cells that have been treated either with an appropriate dilution of the placebo buffer or simply with phosphate buffered saline.

Another useful keratinocyte proliferation assay is with Alamar Blue. Alamar Blue is a viable blue dye that is metabolized by the mitochondria when added to the culture media. The dye then turns red in tissue culture supernatants. The amounts of the red dye may be directly quantitated by reading difference in optical densities between 570 nm and 600 nm. This reading reflects cellular activities and cell number.

Normal primary dermal keratinocytes (CC-0255, NHEK-Neo pooled) are purchased from Clonetics, Inc. These cells are passage 2. Keratinocytes are grown in complete keratinocyte growth media (CC-3001, KGM; Clonetics, Inc.) until they reach 80% confluency. The cells are trypsinized according to the manufacturer's specification. Briefly, cells are washed twice with Hank's balanced salt solution. 2–3 ml of trypsin is added to cells for about 3–5 min at room temperature. Trypsin neutralization solution is added and cells are collected. Cells are spun at 600×g for 5 min at room temperature and plated into new flasks at 3,000 cells per square centimeter using pre-warmed media.

For the proliferation assay, plate 1,000–2,000 keratinocytes per well of the Corning flat bottom 96-well plates in complete media except for the outermost rows. Fill the outer wells with 200 µl of sterile water. This helps to keep temperature and moisture fluctuations of the wells to the minimum. Grow cells overnight at 37° C. with 5% $CO_2$. Wash cells twice with keratinocyte basal media (CC-3101, KBM, Clonetics, Inc.) and add 100 µl of KBM into each well. Incubate for 24 hours. Dilute growth factors in KBM in serial dilution and add 100 µl to each well. Use KGM as a positive control and KBM as a negative control. Six wells are used for each concentration point. Incubate for two to three days. At the end of incubation, wash cells once with KBM and add 100 µl of KBM with 10% v/v alamarBlue pre-mixed in the media. Incubate for 6 to 16 hours until media color starts to turn red in the KGM positive control. Measure O.D. 570 nm minus O.D. 600 nm by directly placing plates in the plate reader.

Construction of KGF-2 Deletion Mutants

Useful deletion mutants for use in compositions of the present invention can be constructed by the following protocol.

Deletion mutants were constructed from the 5' terminus and 3' terminus of KGF-2 gene using an optimized KGF-2 construct as a template. The deletions were selected based on regions of the gene that might negatively affect expression in *E. coli*. For the 5' deletion the primers listed below were used as the 5' primer. These primers contain the indicated restriction site and an ATG to code for the initiator methionine. The KGF-2 (FGF-12) 208 amino acid 3' HindIII primer was used for the 3' primer. PCR amplification for 25 rounds was performed using standard conditions. The products for the KGF-2 36aa/208aa deletion mutant were restricted BspHI for the 5' site and HindIII for the 3' site and cloned into the pQE60 which has bee digested with BspHI and HindIII. All other products were restricted with NcoI for the 5' restriction enzyme and HindIII for the 3' site, and cloned into the pQE60 which had been digested with NcoI and HindIII. For KGF-2 (FGF-12), 36aa/1 53aa and 128aa 3'HindIII was used as the 3' primer with FGF-12 36aa/208aa as the 5' primer. For FGF-12 62aa/153aa, 128aa 3' HindIII was used as the 3' primer with FGF-12 62aa/208aa as the 5' primer. The nomenclature of the resulting clones indicates the first and last amino acid of the polypeptide that results from the deletion. For example, KGF-2 36aa/153aa indicates that the first amino acid of the deletion mutant is amino acid 36 and the last amino acid is amino acid 153 of KGF-2. The construction of these KGF-2 deletion mutants are also described in U.S. application Ser. Nos. 08/910,875, and 09/023,082 and are herein incorporated by reference. Further, as indicated in below, each mutant has N-terminal Met added thereto. However, the KGF-2 deletion polypeptides used in the formulations according to the present invention may or may not have the N-terminal methionine, preferably the polypeptide will be lacking the N-terminal methionine.

Sequences of the Deletion Primers:

FGF12 36aa/208aa:
5'BsphI GGACCCTCATGACCTGCCAG-GCTCTGGGTCAGGAC (SEQ ID NO:3)

FGF12 63aa/208aa: 5' NcoI GGACAGCCATGGCTG-GTCGTCACGTTCG (SEQ ID NO:4)

FGF12 77aa/208aa: 5' NcoI GGACAGCCATGGTTCGT-TGGCGTAAACTG (SEQ ID NO:5)

FGF12 93aa/208aa: 5' NcoI GGACAGCCATG-GAAAAAAACGGTAAAGTTTC (SEQ ID NO:6)

FGF12 104aa/208aa: 5' NcoI GGACCCCCATG-GAGAACTGCCCGTAGAGC (SEQ ID NO:7)

FGF12 123aa/208aa: 5' NcoI GGACCCCCATGGT-CAAAGCCATTAACAGCAAC (SEQ ID NO:8)

FGF12 138aa/208aa: 5' NcoI GGACCCCCATGGG-GAAACTCTATGGCTCAAAAG (SEQ ID NO:9)

FGF12 3' HindIII: (Used for all above deletion clones) CTGCCCAAGCTTATTATGAGTGTACCAC-CATTGGAAG (SEQ ID NO: 10)

FGF12 36aa/153aa: 5' BsphI (as above)

3' HindIII CTGCCCAAGCTTATTACTTCAGCTTA-CAGTCATTGT (SEQ ID NO:11)

FGF12 63aa/153aa: 5NcoI and 3HindIII, as above.

Construction of N-terminal deletion mutant KGF-2 Δ33

Construction of KGF-2 Δ33 in pQE6

To permit Polymerase Chain Reaction directed amplification and sub-cloning of KGF2Δ33 into the *E. coli* protein expression vector, pQE6, two oligonucleotide primers (5952 and 19138) complementary to the desired region of KGF2 were synthesized with the following base sequence.

Primer 5952: 5' GCGGCACATGTCTTACAACCACCT-GCAGGGTG 3'(SEQ ID NO:12)

Primer 19138: 5' GGGCCCAAGCTTATGAGTGTAC-CACCAT 3' (SEQ ID NO: 13)

In the case of the N-terminal primer (5952), an AflIII restriction site was incorporated, while in the case of the C-terminal primer (19138) a HindIII restriction site was incorporated. Primer 5952 also contains an ATG sequence adjacent and in frame with the KGF2 coding region to allow translation of the cloned fragment in E. coli, while primer 19138 contains two stop codons (preferentially utilized in E. coli) adjacent and in frame with the KGF2 coding region which ensures correct translational termination in E. coli.

The Polymerase Chain Reaction was performed using standard conditions well known to those skilled in the art and the nucleotide sequence for the mature KGF-2 (aa 36-208) as template. The resulting amplicon was restriction digested with AflIII and HindIII and subcloned into NcoI/HindIII digested pQE6 protein expression vector.

Construction of KGF-2 Δ33 in pHE1

To permit Polymerase Chain Reaction directed amplification and subcloning of KGF2Δ33 into the E. coli expression vector, pHE1, two oligonucleotide primers (6153 and 6150) corresponding to the desired region of KGF2 were synthesized with the following base sequence.

Primer 6153: 5' CCGGCGGATCCCATATGTCTTA-CAACCACCTGCAGG 3' (SEQ ID NO:14)

Primer 6150:5' CCGGCGGTACCTTATTATGAGTG-TACCACCATTGG3' (SEQ ID NO: 15)

In the case of the N-terminal primer (6153), an NdeI restriction site was incorporated, while in the case of the C-terminal primer (6150) an Asp718 restriction site was incorporated. Primer 6153 also contains an ATG sequence adjacent and in frame with the KGF2 coding region to allow translation of the cloned fragment in E. coli, while primer 6150 contains two stop codons (preferentially utilized in E. coli) adjacent and in frame with the KGF2 coding region which ensures correct translational termination in E. coli.

The Polymerase Chain Reaction was performed using standard conditions well known to those skilled in the art and the nucleotide sequence for the mature KGF-2 (aa 36-208) as template. The resulting amplicon was restriction digested with NdeI and Asp718 and subcloned into NdeI/Asp718 digested pHE1 protein expression vector.

Nucleotide sequence of KGF-2 Δ33

ATGTCTTACAACCACCTGCAGGGT-GACGTTCGTTGGCGTAAACTGTT
CTCTTTCACCAAATACTTCCTGAAAATCGAAAA
AAACGGTAAAGTTTCTGGGACCAAGAAG-GAGAACTGCCCGTACAGC
ATCCTGGAGATAACATCAGTAGAAATCGGAGTTG
TTGCCGTCAAAGCCATTAACAGCAAC-TATTACTTAGCCATGAACAA
GAAGGGGAAACTCTATGGCTCAAAA-GAATTTAAC
AATGACTGTAAGCTGAAGGAGAGGATA-GAGGAAAATGGATACAAT
ACCTATGCATCATTTAACTGGCAGCAT-AATGGGAG
GCAAATGTATGTGGCATTGAATG-GAAAAGGAGCTCCAAGG
AGAGGACAGAAAACACGAAGGAAAAA-CACCTCTGCTCACTTTCTTC
CAATGGTGGTACACTCATAA (SEQ ID NO: 16)

Amino Acid sequence of KGF-2 Δ33:

MSYNHLQGDVRWRKLFSFTKY-FLKEEKNGKVSGTKKENCPYSILEITSV
EIGWAVKAINSNYYLAMNKKGKLYG-SKEFNNDCKLKERIEENGYNT
YASFNWQHNGRQMYVALNGKGAPRRGQK-TRRKNTSAHFLPMVVHS (SEQ ID NO: 17)

B. Construction of an Optimized KGF-2 Δ33 Polynucleotide Sequence In order to increase the expression levels of KGF2Δ33 in E. coli, the codons of the complete gene were optimized to match those most highly used in E. coli. As the template utilized to generate the KGF2Δ33 was codon optimized within the N-terminal region, the C-terminal amino acids (84–208) required optimization.

Firstly, amino acids 172–208 were codon optimized to generate KGF2Δ33(s172-208). This was achieved by an overlapping PCR strategy. Oligonucleotides PM07 and PM08 (corresponding to amino acids 172–208) were combined and annealed together by heating them to 70° C. and allowing them to cool to 37° C. The annealed oligonucleotides were then utilized as template for a standard PCR reaction which was directed by primers PM09 and PM10. In a separate PCR reaction following standard conditions well known to those skilled in the art and using KGF2Δ33 as template, oligonucleotides PM05 (which overlaps with the Pst1 site within coding region of KGF2) and PM11 were used to amplify the region of KGF2 corresponding to amino acids 84–172. In a third PCR reaction, the product of the first PCR reaction (corresponding to codon optimized amino acids 172–208) and the product of the second PCR reaction (corresponding to codon non-optimized amino acids 84–172) were combined and used as template for a standard PCR reaction directed by oligonucleotides PM05 and PM10. The resulting amplicon was digested with Pst1/HindIII and sub-cloned into Pst1/HindIII digested pQE6KGF2Δ33, effectively substituting the corresponding non codon optimized region, and creating pQE6KGF2Δ33(s172-208).

To complete the codon optimization of KGF2, a synthetic gene codon optimized for the region of KGF2 corresponding to amino acids 84-172 was generated utilizing overlapping oligonucleotides. Four oligonucleotides (PM31, PM32, PM33 and PM 34) were combined and seven cycles of the following PCR was performed: 94° C., 30 secs; 46.5° C., 30 secs; and 72° C., 30 secs.

A second PCR reaction directed by primers PM35 and PM36 was then performed following standard procedures, utilizing 1 μl of the first PCR reaction as template. The resulting codon optimized gene fragment was then digested with Pst1/Sal1 and subcloned into Pst1/Sal1 digested pQE6KGF2Δ33(s172-208) to create a fully optimized KGF2 encoding gene, pQE6KGF2Δ33s.

To create an alternative E. coli protein expression vector, KGF2Δ33s was PCR amplified utilising primers PM102 and PM130 on pQE6KGF2Δ33s. The resulting amplicon was digested with NdeI and EcoRV and subcloned into the pHE1 expression vector which had been digested with NdeI and Asp718 (blunt ended) to create pHE1Δ33s.

Oligonucleotide Sequences used in construction of codon optimized KGF-2 Δ33s:

PM05: CAACCACCTGCAGGGTGACG (SEQ ID NO: 18)

PM07: AACGGTCGACAAATGTATGTGGCACT-GAACGGTAAAGGTG CTCCACGTCGTGGTCA-GAAAACCCGTCGTAAAAACACC (SEQ ID NO: 19)

PM08: GGGCCCAAGCTTAAGAGTGTACCACCAT-TGGCAGAAAGT GAGCAGAGGTGTTTTTAC-GACGGGTTTTCTGACCACG (SEQ ID NO:20)

PM09: GCCACATACATTTGTCGACCGTT (SEQ ID NO:21)

PM10: GGGCCCAAGCTTAAGAGTG (SEQ ID NO:22)

PM11:GCCACATACATTTGTCGACCGTT (SEQ ID NO:23)

PM31:CTGCAGGGTGACGTTCGTTGGCGTAAACT GTTCTCCTTCACCA AATACTTCCTGAAAATC-GAAAAAAACGGTAAAGTTTCTGGTACCAA G (SEQ ID NO:24)

PM32:AGCTTTAACAGCAACAACACCGATTTCAA CGGAGGTGATTTC CAGGATGGAG-TACGGGCAGTTTTCTTTCTTGGTACCA-GAAACTTTAC C (SEQ ID NO:25)

PM33:GGTGTTGTTGCTGTTAAAGCTATCAACT CCAACTACTACCTGG CTATGAACAAGAAAGG-TAAACTGTACGGTTCCAAAGAATTTAACAA C (SEQ ID NO:26)

PM34:GTCGACCGTTGTGCTGCCAGTTGAAGG AAGCGTAGGTGTTGT AACCGTTTTCTTC-GATACGTTCTTTCAGTTTACAGTCGT-TGTTAAATT CTTTGGAACC (SEQ ID NO:27)

PM35: GCGGCGTCGACCGTTGTGCTGCCAG (SEQ ID NO:28)

PM36: GCGGCCTGCAGGGTGACGTTCGTTGG (SEQ ID NO:29)

PM102: CCGGCGGATCCCATATGTCTTACAAC-CACCTGCAGG (SEQ ID NO:30)

PM130: CGCGCGATATCTTATTAAGAGTGTAC-CACCATTG (SEQ ID NO:31)

Nucleotide sequence of KGF-2 Δ33(s172-208):
ATGTCTTACAACCACCTGCAGGGT-GACGTTCGTTGGCGTAAACTGTT
CTCCTTCACCAAATACTTCCTGAAAATCGAAAA
AAACGGTAAAGTTTCTGGTACCAAGAAA-GAAAACTGCCCGTACTCC
ATCCTGGAAATCACCTCCGTTGAAATCGGTGTTG
TTGCTGTTAAAGCTATCAACTCCAAC-TACTACCTGGCTATGAACAAG
AAAGGTAAACTGTACGGTTCCAAAGAATTTAAC
AACGACTGTAAACTGAAAGAACGTATC-GAAGAAACGGTTACAACA
CCTACGCTTCCTTCAACTGGCAGCACAACGGTCG
ACAAATGTATGTG
(iCACTGAACGGTAAAGGTGCTCCACGTCGTGGT
CAGAAAACCCGTCGTAAAAACACCTCTGCTC
ACTTTCTGCCAATGGTGGTACACTCTTAA (SEQ ID NO:32)

Amino Acid Sequence of KGF-2 Δ33(s172-208):
MSYNHLQGDVRWRKLFSFTKYFLK-IEKNGKVSGTKKENCPYSILEITSV EIGWAV-KAINSNYYLAMNKKGKLYGSKEFNNDCK-LKERIEENGYNT YASFNWQHNGRQMYVALNGKGAPRRGQK-TRRKNTSAHFLPMVVHS (SEQ ID NO:33)

EXAMPLES

Example 1

KGF-2 Liquid Formulation

The following ingredients were mixed to create a liquid KGF-2 Δ33 formulation is a liquid that is stored at −20° C.

2 mg/ml KGF-2 Δ33 polypeptide,
20 mM sodium acetate,
125 mM sodium chloride,
1 mM EDTA,
Water, pH 6.2.

This formulation retained its in vitro bioactivity for up to 10 months at storage conditions at or below 2 to 8° C. The bioactivity at 10 months is shown in FIG. 3. This formulation retained all its physico-chemical properties for up to 11 months at storage conditions at or below Bioactivity was measured using a cell proliferation assay as follows BaF3 cells, were routinely grown and maintained in RPMI 1640 medium containing 10 % NBCS, 10% WEHI cell conditioned medium, 2 mM glutamine, 600 $\mu$g/ml GENETICIN, 1 $\mu$l β mercaptoethanol/500 ml growth medium, 50 units penicillin and 50 $\mu$g/ml streptomycin (Ornitz, D., M. et al (1996) *J. Biol. Chem.* 271:15292–15297). For cell proliferation assays, BaF3 cells were harvested by centrifugation and washed with Basal medium (this has the same composition as the growth medium, but contains no WEHI conditioned medium and is supplemented with 1 $\mu$g/ml heparin). Following this operation the cells were resuspended in basal medium and 22,000 cells/180 $\mu$; were plated/well in a 96 well cell culture cluster dish. Appropriate dilutions (10×higher than the required final concentration) of KGF 2 were made in PBS in another 96 well plate and added to the cells to a final volume of 200 $\mu$l. The cell plates were incubated in a 37° C., 5 % $CO_2$ incubator for 36–40 hr. and 0.5 $\mu$Ci methyl - $^3$H thymidine in 50 $\mu$L basal medium was added to each well. The plates were incubated for another 5 hr. in the incubator and cells were harvested by filtration on a glass fiber filter using a Tomtec Harvester 96. Incorporated thymidine was counted on a Wallac β plate scintillation counter.

Example 2

KGF-2 Lyophilized Formulation

The following ingredients were mixed to create a KGF-2 Δ33 lyophilized formulation.

10 mg/ml KGF-2 Δ33,
10 mM sodium citrate,
20 mM sodium chloride,
1 mM EDTA,
7% w/v sucrose,
water (removed upon lyophiliztion)
pH 6.2.

This formulation retained its in vitro bioactivity for up to 9 months at storage conditions at or below 45° C. The bioactivity at 9 months is shown in FIG. 4. Bioactivity was measured using the cell proliferation assay detailed in Example 1. Reverse-phase HPLC demonstrated that the formulation retained its physio-chemical properties for up to 8 months at temperatures of at or below 45° C. and 75% relative humidity.

Example 3

KGF-2 in a Thickened Formulation

The following ingredients were mixed to create a KGF-2 Δ33 thickened formulation.

2 mg/ml KGF-2 Δ33,
10 mM sodium citrate,
20 mM sodium chloride,
1 mM EDTA,
7% w/v sucrose,
1.25% carboxy methyl cellulose,
water
pH 6.2.

This formulation is prepared by adding KGF-2 Δ33 polypeptide to the carboxy methyl cellulose solution. The viscosity of the resulting formulation was about 250 cps as determined by rotating spindle viscometer. The KGF-2 polypeptide retained bioactivity in the presence of carboxy methyl cellulose. Bioactivity of the formulation was assayed using the cell proliferation assay detailed in Example 1.

Example 4

KGF-2 in a Gel Formulation

The following ingredients were mixed to create a KGF-2 Δ33 gel formulation.

2 mg/ml KGF-2 Δ33,
10 mM sodium citrate,
20 mM sodium chloride,
1 mM EDTA,
7% w/v sucrose,
16% Pluronic F127,
water
pH 6.2.

KGF-2 Δ33 is added to a Pluronic solution at about 2° C. to about 8° C. The viscosity of the resulting formulation was about 50 cps at 20° C. and solid at about 37° C. KGF-2 retained bioactivity in the presence of Pluronic F127 as measured by the cell proliferation assay detailed in Example 1.

Example 5

Activation of KGF 2 by Monothioglycerol

KGF-2 Δ33 protein stock formulations (0.1 to 2.0 mg/ml) were prepared with or without monothioglycerol (MTG).

The protein formulations were diluted in 1×phosphate buffered saline (PBS) at pH 7.2 to attain the required concentrations for use in the cell proliferation assays.

Cell culture

BaF32b cells, were routinely grown and maintained in RPMI 1640 medium containing 10% NBCS, 10% WEHI cell conditioned medium, 2 mM glutamine, 600 μg/ml GENETICIN, 1 μl β mercaptoethanol/500 ml growth medium, 50 units penicillin and 50 μg/ml streptomycin (Ornitz, D., M. et al (1996) *J. Biol. Chem.* 271:15292–15297).

Cell Proliferation Assays

For cell proliferation assays, BaF32b cells were harvested by centrifugation and washed with Basal medium (this has the same composition as the growth medium, but contains no WEHI conditioned medium and is supplemented with 1 μg/ml heparin). Following this operation the cells were resuspended in basal medium and 22,000 cells/180 μl were plated/well in a 96 well cell culture cluster dish. Appropriate dilutions (10×higher than the required final concentration) of KGF 2 were made in PBS in another 96 well plate and added to the cells to a final volume of 200 μl. The cell plates were incubated in a 37° C., 5% $CO_2$ incubator for 36–40 hr. and 0.5 μCi methyl -$^3$ H thymidine in 50 μl basal medium was added to each well. The plates were incubated for another 5 hr. in the incubator and cells were harvested by filtration on a glass fiber filter using a Tomtec Harvester 96. Incorporated thymidine was counted on a Wallac β plate scintillation counter.

Results

A. Effect of MTG concentration on KGF-2 activity

The cell proliferation assay was carried out with KGF-2 exposed to different concentrations of monothioglycerol (MTG). Control samples contained no excipient. With MTG, stimulation of KGF-2 activity was observed with various concentrations of MTG is shown in FIG. 5. The increase in activity was between 10–150% of control depending on the concentration of MTG used. This enhancement of cell proliferation activity was not observed with other members of this growth factor family. From these observations, it was concluded that stimulation of KGF-2 activity by MTG was quite specific.

Conclusions

Monothioglycerol appears to specifically stimulate the in vitro cell proliferation activity of KGF-2.

Example 6

KGF-2 Gel Formulation with Citrate

The following ingredients were mixed to create a KGF-2 formulation is a liquid at room temperature and that subsequently gels upon application to skin.

20 mM sodium citrate,
125 mM sodium chloride,
1 mM disodium EDTA,
17% Pluronic 127, pH 6.0,
water.

Example 7

KGF-2 Gel Formulation with Acetate

The following ingredients were mixed to create a KGF-2 formulation that can gel upon application to skin.

20 mM sodium acetate,
125 mM sodium chloride,
1 mM disodium EDTA,
17% Pluronic 127, pH 6.0,
water.

Example 8

Liquid KGF-2 Formulations

The suitability of sodium citrate as a buffer in which to maintain KGF-2 Δ33 was evaluated in four separate formulations, and at three separate pHs: pH 5.0, pH 5.5 and pH 6.0.

Formulations:

A. KGF-2 Δ33 1 or 2 mg/ml
20 mM sodium citrate,
125 mM sodium chloride,
1 mM disodium EDTA,
water.

B. As in "A" above, further including 1% glycerol.

C. As in "A" above, further including 0.05% methionine.

D. As in "A" above, further including 1% monothioglycerol.

The concentration of KGF-2 Δ33 was 1 and 2 mg/ml in all of the above formulations.

2. Lyophilization formulation

KGF-2 Δ33 was lyophilized in the presence of one of three bulking agents: mannitol, sucrose and trehalose.

Formulations:

A. 10 mM sodium citrate, 20 mM sodium chloride, 1 mM disodium EDTA and 4% mannitol, pH 6.0

B. 10 mM sodium citrate, 20 mM sodium chloride, 1 mM disodium EDTA and 7% sucrose, pH 6.0

C. 10 mM sodium citrate, 20 mM sodium chloride, 1 mM disodium EDTA and 8% trehalose, pH 6.0

The concentration of KGF-2 polypeptide was 3 mg/ml and 8 mg/ml. Evaluation parameters were RP-HPLC, SDS-PAGE, appearance, before and following reconstitution with water.

3. 10 mg/ml KGF-2 lyophilization Whether the formulation will permit lyophilization of the protein at 10 mg/ml was assessed as well as the protein's subsequent stability after reconstitution.

Formulation:

10 mM sodium citrate, 20 mM sodium chloride, 1 mM disodium EDTA and 4% mannitol, pH 6.0.

The lyophilized products were reconstituted with water or water containing 1% monothioglycerol.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A pharmaceutical composition, comprising:

(a) a KGF-2 polypeptide in a concentration range of about 0.02 to about 40 mg/ml (w/v);

(b) a buffer having a buffering capacity of about pH 5.0 to about pH 8.0 at a concentration range of about 5 mM to about 50 mM; and (c) a diluent to bring the composition to a designated volume;

or a reaction product of (a), (b), (c) or any combination thereof formed by admixing the ingredients of said composition together.

2. The pharmaceutical composition of claim 1, further comprising:

(d) a chelating agent at a concentration range of about 0.1 mM to about 10 mM; and (e) NaCl at a concentration range of about 0.01 mM to about 150 mM.

3. The pharmaceutical composition of claim 1, further comprising one of:

(f) about 0.5% to about 2% w/v glycerol, (g) about 0.1% to about 1% w/v methionine, or (h) about 0.1% to about 2% w/v monothioglycerol.

4. The pharmaceutical composition of claim 1, wherein said KGF-polypeptide is present in a concentration range of about 0.05 to about 30 mg/ml (w/v).

5. The pharmaceutical composition of claim 4, wherein said KGF-polypeptide is present in a concentration range of about 0.1 to about 20 mg/ml (w/v).

6. The pharmaceutical composition of claim 5, wherein said KGF-polypeptide is present in a concentration range of about 0.2 to 4 mg/ml.

7. The pharmaceutical composition of claim 1, wherein said KGF-2 polypeptide is Ser (69)—Ser (208) of KGF-2.

8. The pharmaceutical composition of claim 1, wherein said diluent is water.

9. The pharmaceutical composition of claim 2, wherein said chelating agent is ethylenediamine tetraacetic acid at a concentration of about 1 mM, and said NaCl is present at a concentration of about 125 mM.

10. The pharmaceutical composition of claim 1, wherein said pH is from about pH 5.5 to about pH 6.5.

11. The pharmaceutical composition of claim 10, wherein said pH is about pH 6.2.

12. The pharmaceutical composition of claim 1, wherein said buffer is selected from the group consisting of phosphonic, acetic, aconitic, citric, glutaric, malic, succinic carbonic acid, and an alkali or alkaline earth salt thereof.

13. The pharmaceutical composition of claim 12, wherein said buffer is a phosphate, acetate or citrate salt.

14. The pharmaceutical composition of claim 13, wherein said buffer is a citrate salt.

15. The pharmaceutical composition of claim 1, wherein said buffer is present in a concentration range of about 5 mM to about 30 mM.

16. The pharmaceutical composition of claim 15, wherein said buffer is a citrate salt present in a concentration of from about 10 mM to about 20 mM.

17. The pharmaceutical composition of claim 1, further comprising a stabilizing amount of one or more of (a) an antioxidant or (b) a thiol-compound.

18. The pharmaceutical composition of claim 1, wherein said composition is maintained at a temperature at or below −20° C.

19. The pharmaceutical composition of claim 1, comprising:

(a) 2 mg/ml Ser (69)—Ser (208) of KGF-2polypeptide (w/v);

(b) 20 mM sodium acetate;

(c) 125 mM NaCl;

(d) 1 mM ethylenediamine tetraacetic acid; and (e) water as diluent, or a reaction product of (a), (b) or (c) or any combination thereof formed by admixing the ingredients of said composition together.

20. The pharmaceutical composition of claim 19, wherein said KGF-2 polypeptide is selected from the group consisting of Ser (69)—Ser (208) of KGF-2 having an N-terminal methionine, Ser (69)—Ser (208) of KGF-2 lacking an N-terminal methionine, and a mixture thereof.

21. A pharmaceutical composition, comprising:

(a) a KGF-2 polypeptide in a concentration range of about 0.02 to about 40 mg/ml (w/v);

(b) a buffer having a buffering capacity of about pH 5.0 to about pH 8.0 at a concentration range of about 5 mM to about 50 mM;

(c) a bulking agent; and (d) a to bring the composition to a designated volume;

or a reaction product of (a), (b), (c), (d) or any combination thereof formed by admixing the ingredients of said composition together.

22. The pharmaceutical composition of claim 21, wherein said bulking agent is selected from the group consisting of sucrose, glycine, mannitol, trehalose, and mixtures of two or more of the bulking agents present in any combination thereof in any amount as long as the total amount of the components make up 100% of the bulking agent.

23. The pharmaceutical composition of claim 21, further comprising:

(e) a chelating agent at a concentration range of about 0.1 mM to about 10 mM; and (f) NaCl at a concentration range of about 0.01 mM to about 125 mM.

24. The pharmaceutical composition of claim 22, wherein said bulking agent is sucrose or a mixture of sucrose and glycine present in any combination thereof in any amount as long as the total amount of sucrose and glycine make up 100% of the bulking agent.

25. The pharmaceutical composition of claim 22, wherein said bulking agent is present in a concentration of about 2% to about 10% w/v.

26. The pharmaceutical composition of claim 22, wherein said bulking agent is 5% mannitol, 7% sucrose, 8% trehalose, or 2% glycine +0.5% sucrose.

27. The pharmaceutical composition of claim 21, wherein said pH is about pH 6.2.

28. The pharmaceutical composition of claim 21, wherein said diluent is water.

29. The pharmaceutical composition of claim 21, wherein said buffer is selected from the group consisting of phosphonic, acetic, aconitic, citric, glutaric, malic, succinic carbonic acid, and an alkali or alkaline earth salt thereof.

30. The pharmaceutical composition of claim 29, wherein said buffer is a phosphate or citrate salt.

31. The pharmaceutical composition of claim 30, wherein said buffer is a citrate salt.

32. The pharmaceutical composition of claim 21, wherein said KGF polypeptide is Ser (69)—Ser (208) of KGF-2.

33. The pharmaceutical composition of claim 32, wherein said KGF-2 Δ33 polypeptide is selected from the group consisting of Ser (69)—Ser (208) of KGF-2 having an N-terminal methionine, Ser (69)—Ser (208) of KGF-2 lacking an N-terminal methionine, and a mixture thereof.

34. The pharmaceutical composition of claim 21, wherein said buffer is added in a concentration from about 5 mM to about 50 mM.

35. The pharmaceutical composition of claim 34, wherein said buffer is citrate at a concentration of about 10 mM.

36. The pharmaceutical composition of claim 21, further including a stabilizing amount of one or more of (g) an antioxidant, or (h) a thiol-compound.

37. A pharmaceutical composition, comprising:
(a) a KGF-2 polypeptide in a concentration range of about 0.02 to about 40 mg/ml (w/v);
(b) citric acid or a pharmaceutically acceptable salt thereof, at a concentration range of about 5 mM to about 20 mM;
(c) NaCl at a concentration range of about 0.01 mM to about 125 mM;
(d) ethylenediamine tetraacetic acid at a concentration range of about 0.1 mM to about 10 mM;
(e) one or more of sucrose, mannitol, glycine or trehalose at a concentration range of about 2% w/v to about 15% w/v; and
(f) water.

38. The pharmaceutical composition of claim 37, wherein said KGF-2 polypeptide is present at a concentration of about 2 mg/ml, about 4 mg/ml, or about 10 mg/ml.

39. The pharmaceutical composition of claim 1, further comprising a thickening agent in an amount effective to raise the viscosity to about 50 to about 10,000 centipoise.

40. The pharmaceutical composition of claim 40, wherein said thickening agent is present in an amount effective to raise the viscosity to about 50 to about 1,000 centipoise.

41. The pharmaceutical composition of claim 40, wherein said thickening agent in an amount effective to raise the viscosity to about 200 to about 300 centipoise.

42. The pharmaceutical composition of claim 21, further comprising a thickening agent in an amount effective to raise the viscosity to about 50 to about 10,000 centipoise.

43. The pharmaceutical composition of claim 39, wherein said thickening agent is present in a concentration of 0 to 5% (w/w).

44. The pharmaceutical composition of claim 39, wherein said thickening agent is a water soluble etherified cellulose or a high molecular weight polymer of acrylic acid cross-linked with allylsucrose or an allyl ether of pentaerythritol.

45. The pharmaceutical composition of claim 44, wherein said etherified cellulose is an alkyl cellulose, hydroxyalkyl cellulose, carboxyalkyl cellulose or alkylhydroxyalkyl cellulose.

46. The pharmaceutical composition of claim 39, wherein said etherified cellulose is methylcellulose, hydroxyethyl cellulose, hydroxy propyl cellulose, hydroxy propyl methylcellulose, or carboxymethyl cellulose.

47. The pharmaceutical composition of claim 45, wherein said etherified cellulose derivative has a molecular weight of about 50,000 to about 700,000 and is present in a concentration of about 0 to about 20% by weight.

48. The pharmaceutical composition of claim 47, wherein said etherified cellulose derivative has a molecular weight of about 80,000 to about 240,000 and is present in a concentration of about 2% to about 8% by weight.

49. The pharmaceutical composition of claim 42, wherein said buffer is citrate in a concentration of about 10 mM to about 50 mM.

50. The pharmaceutical composition of claim 49, wherein said buffer is citrate in a concentration of about 10 mM to about 20 mM citrate.

51. The pharmaceutical composition of claim 49, wherein said bulking agent is sucrose in a concentration of about 0.01% to about 5% sucrose.

52. The pharmaceutical composition of claim 51, wherein said thickening agent is added directly to a liquid formulation and thereafter lyophilized.

53. The pharmaceutical composition of claim 51, wherein said thickening agent is added to a lyophilized formulation by reconstituting said formulation by adding a suitable diluent having a thickening agent dissolved therein.

54. A thickened KGF-2 polypeptide solution composition formed by mixing:
(a) a KGF-2 polypeptide in a concentration range of about 0.01 µg/ml to about 10 mg/ml;
(b) about 10 mM to about 500 mM sodium citrate buffer;
(c) about 0.01 to about 150 mM NaCl;
(d) 1 mM ethylenediamine tetraacetic acid;
(e) about 0.1 to about 7% sucrose; and
(f) about 0.75 to about 1.5% (w/w) carboxy methyl cellulose or about 0.5 to about 1.5% hydroxy propyl methyl cellulose or about 0.25 to about 0.75% hydroxy ethyl cellulose or about 0 to 1% carbomer or any combination thereof.

55. The composition of claim 1, further comprising a gelling agent in an amount effective to raise the viscosity to about 0.1 to about 10,000 centipoise at room temperature.

56. The composition of claim 21, further comprising a gelling agent in an amount effective to raise the viscosity to about 0.1 to about 10,000 centipoise at room temperature.

57. The composition of claim 55, wherein said gel forming agent is a water-soluble polymer capable of forming a viscous aqueous solution, or non-water soluble, water-swellable polymer capable of forming a viscous solution.

58. The composition of claim 57, wherein said gel forming agent is a high molecular weight polymer selected from the group consisting of vinyl polymer, polyoxyethylene-polyoxypropylene copolymer, polysaccharide, protein, poly (ethylene oxide), acrylamide polymer or a salt thereof.

59. The composition of claim 58, wherein said gel forming agent is (1) a vinyl polymer selected from the group consisting of polyacrylic acid, polymethacrylic acid, polyvinyl pyrrolidone polyvinyl alcohol and salts and esters thereof; or (2) a polysaccharide selected from the group consisting of a cellulose derivative, a glycosaminoglycan, agar, pectin, alginic acid, dextran, α-amylose, amylopectin, chitosan, and salts esters thereof.

60. The composition of claim 58, wherein said gel forming agent is a glycosaminoglycan selected from the group consisting of hyaluronic acid, chondroitin, chondroitin-4-sulfate, heparan sulfate, heparin and salts and esters thereof.

61. The composition of claim 60, wherein said glycosaminoglycan is present in combination with collagen, gelatin, or fibronectin.

62. The composition of claim 58, wherein said gel forming agent is an acrylamide polymer selected from the group consisting of a polyacrylamide or a polymethacrylamide.

63. The composition of claim 58, wherein said gel forming agent is a polyoxyethylene-polyoxypropylene block copolymer.

64. The composition of claim 63, which comprises about 10 to about 60% by weight of a polyoxyethylene-polyoxypropylene block copolymer having an average molecular weight of about 500 to 50,000.

65. The composition of claim 64, which comprises about 14 to about 18% by weight of a polyoxyethylene-polyoxypropylene block copolymer having a molecular weight in the range 1,000 to 15,000.

66. The composition of claim 65, wherein said gel forming agent is a polyoxyethylene-polyoxypropylene block copolymer having an average molecular weight of 12,600 or 14,600.

67. The composition of claim 1, wherein said KGF-2 polypeptide is present in a concentration of about 0.01 mg/ml to about 10 mg/ml.

68. The composition of claim 55, wherein said composition is formed by mixing:
  (a) a KGF-2 polypeptide, in a final calculated concentration of 0.01 mg/ml to about 10 mg/ml;
  (b) an effective amount of a buffering agent;
  (c) about 10% to about 60% by weight of a polyoxyethylene-polyoxypropylene block copolymer having an average molecular weight of about 500 to 50,000; and
  (d) a diluent.

69. The composition of claim 68, wherein polyoxyethylene-polyoxypropylene block copolymer is present at a concentration of about 14% to about 18%.

70. A KGF-2 gel formulation, comprising:
  (a) a KGF-2 polypeptide in a concentration range of about 0.01 mg/ml to about 10 mg/ml;
  (b) about 10 mM to about 500 mM sodium citrate;
  (c) about 0.01 mM to about 150 mM NaCl;
  (d) about 1 mM ethylenediamine tetraacetic acid;
  (e) about 0.1% to about 7% sucrose; and
  (f) about 14% to about 18% of a polyoxypropylene-polyoxyethylene block copolymer having an average molecular weight of 12,600;
  wherein the pH of said formulation is about pH 6.2.

71. A KGF-2 gel formulation, comprising:
  (a) a KGF-2 polypeptide at a concentration range of about 0.01 mg/ml to about 10 mg/ml (w/v),
  (b) sodium citrate at a concentration range of about 5 mM to about 20 mM;
  (c) about 10% to about 25% (w/v), of a polyoxyethylene polyoxypropylene copolymer having an average molecular weight of 12,600; and
  (d) water to volume.

72. The gel formulation of claim 71, further comprising:
  (a) ethylenediamine tetraacetic acid at a concentration range of about 0.1 mM to about 10 mM; and
  (b) NaCl at a concentration range of about 0.01 mM to about 125 mM.

73. The pharmaceutical composition of claim 1, wherein said KGF-2 polypeptide is a N-terminal deletion selected from the group consisting of Ala (63)—Ser (208) and Ser (69)—Ser (208).

74. The pharmaceutical composition of claim 73, wherein said KGF-2 polypeptide has an N-terminal methionine, lacks an N-terminal methionine, or is a mixture thereof.

75. The pharmaceutical composition of claim 1, wherein said KGF-2 polypeptide is a N-terminal or C-terminal deletion mutant selected from the group consisting of Ala (39)—Ser (208); Pro (47)—Ser (208); Val (77)—Ser (208); Glu (93)—Ser (208); Glu (104)—Ser (208); Val (123)—Ser (208); Gly (138)—Ser (208); Met (1), Thr (36); and Cys (37)—Lys (153).

76. The pharmaceutical composition of claim 75, wherein said KGF-2 polypeptide has an N-terminal methionine, lacks an N-terminal methionine, or is a mixture thereof.

77. The pharmaceutical composition of claim 7, wherein said polypeptide is selected from the group consisting of Ser (69)—Ser (208) of KGF-2 having an N-terminal methionine, Ser (69)—Ser (208) of KGF-2 lacking an N-terminal methionine, and a mixture thereof.

78. A pharmaceutical composition produced by removing, by lyophilization, over 90% of the water from a mixture comprising:
  (a) a KGF-2 polypeptide in a concentration range of about 0.02 to about 40 mg/ml (w/v);
  (b) a buffer having a buffering capacity of about pH 5.0 to about pH 8.0 at a concentration range of about 5 mM to about 50 mM;
  (c) a bulking agent; and
  (d) water to bring the composition to a designated volume;
  or a reaction product of (a), (b), (c), (d) or any combination thereof formed by admixing the ingredients of said composition together.

79. A pharmaceutical composition, produced by removing, by lyophilization, over 90% of the water from a mixture comprising:
  (a) a KGF-2 polypeptide in a concentration range of about 0.02 to about 40 mg/ml (w/v);
  (b) citric acid or a pharmaceutically acceptable salt thereof, at a concentration range of about 5 mM to about 20 mM;
  (c) NaCl at a concentration range of about 0.01 mM to about 125 mM;
  (d) ethylenediamine tetraacetic acid at a concentration range of about 0.1 mM to about 10 mM;
  (e) one or more of sucrose, mannitol, glycine or trehalose at a concentration range of about 2% w/v to about 15% w/v; and
  (f) water.

80. The pharmaceutical composition of claim 78, which is reconstituted with an amount of sterile water effective to maintain isotonic conditions of about 290 mOsm.

81. The pharmaceutical composition of claim 32, wherein said composition is reconstituted in sterile water containing a stabilizing amount of an antioxidant selected from the group consisting of: a) about 0.01% to about 2% w/v monothioglycerol, b) about 0.01% to about 2% w/v ascorbic acid, c) about 0.01% to about 2% w/v methionine or d) combinations thereof.

* * * * *

UNITED STATES PATENT AND TRADEMARK OFFICE
CERTIFICATE OF CORRECTION

PATENT NO.  : 6,238,888 B1
DATED       : May 29, 2001
INVENTOR(S) : Gentz et al.

Page 1 of 1

It is certified that error appears in the above-identified patent and that said Letters Patent is hereby corrected as shown below:

Column 45, claim 19,
Line 56, please delete "KGF-2polypeptide" and insert therein -- KGF-2 polypeptide --.

Column 45, claim 20,
Line 67, please delete "KGF-2".

Column 46, claim 21,
Line 12, please amend "a to bring" to read -- a diluent to bring --.

Column 46, claim 26,
Line 41, please delete "+0.5%" and insert therein -- + 0.5% --.

Column 47, claim 40,
Line 24, please delete "claim 40" and insert therein -- claim 39 --.

Column 50, claim 81,
Line 53, please delete "claim 32" and insert therein -- claim 78 --.

Signed and Sealed this

Ninth Day of April, 2002

Attest:

Attesting Officer

JAMES E. ROGAN
*Director of the United States Patent and Trademark Office*

SEQUENCE LISTING

<160> NUMBER OF SEQ ID NOS: 33

<210> SEQ ID NO 1
<211> LENGTH: 627
<212> TYPE: DNA
<213> ORGANISM: Homo sapiens
<220> FEATURE:
<221> NAME/KEY: CDS
<222> LOCATION: (1)..(624)

<400> SEQUENCE: 1

```
atg tgg aaa tgg ata ctg aca cat tgt gcc tca gcc ttt ccc cac ctg    48
Met Trp Lys Trp Ile Leu Thr His Cys Ala Ser Ala Phe Pro His Leu
 1               5                  10                  15 ccc ggc tgc tgc tgc tgc ttt ttg ttg ctg ttc ttg gtg tct tcc        96
Pro Gly Cys Cys Cys Cys Cys Phe Leu Leu Leu Phe Leu Val Ser Ser
             20                  25                  30 gtc cct gtc acc tgc caa gcc ctt ggt cag gac atg gtg tca cca gag   144
Val Pro Val Thr Cys Gln Ala Leu Gly Gln Asp Met Val Ser Pro Glu
         35                  40                  45 gcc acc aac tct tct tcc tcc tcc ttc tcc tct cct tcc agc gcg gga   192
Ala Thr Asn Ser Ser Ser Ser Ser Phe Ser Ser Pro Ser Ser Ala Gly
     50                  55                  60 agg cat gtg cgg agc tac aat cac ctt caa gga gat gtc cgc tgg aga   240
Arg His Val Arg Ser Tyr Asn His Leu Gln Gly Asp Val Arg Trp Arg
 65                  70                  75                  80 aag cta ttc tct ttc acc aag tac ttt ctc aag att gag aag aac ggg   288
Lys Leu Phe Ser Phe Thr Lys Tyr Phe Leu Lys Ile Glu Lys Asn Gly
                 85                  90                  95 aag gtc agc ggg acc aag aag gag aac tgc ccg tac agc atc ctg gag   336
Lys Val Ser Gly Thr Lys Lys Glu Asn Cys Pro Tyr Ser Ile Leu Glu
            100                 105                 110 ata aca tca gta gaa atc gga gtt gtt gcc gtc aaa gcc att aac agc   384
Ile Thr Ser Val Glu Ile Gly Val Val Ala Val Lys Ala Ile Asn Ser
        115                 120                 125 aac tat tac tta gcc atg aac aag aag ggg aaa ctc tat ggc tca aaa   432
Asn Tyr Tyr Leu Ala Met Asn Lys Lys Gly Lys Leu Tyr Gly Ser Lys
    130                 135                 140 gaa ttt aac aat gac tgt aag ctg aag gag agg ata gag gaa aat gga   480
Glu Phe Asn Asn Asp Cys Lys Leu Lys Glu Arg Ile Glu Glu Asn Gly
```

```
                145                 150                 155                 160
tac aat acc tat gca tca ttt aac tgg cag cat aat ggg agg caa atg        528
Tyr Asn Thr Tyr Ala Ser Phe Asn Trp Gln His Asn Gly Arg Gln Met
                165                 170                 175 tat gtg gca ttg aat gga aaa gga gct cca agg aga gga cag aaa aca        576
Tyr Val Ala Leu Asn Gly Lys Gly Ala Pro Arg Arg Gly Gln Lys Thr
                180                 185                 190 cga agg aaa aac acc tct gct cac ttt ctt cca atg gtg gta cac tca        624
Arg Arg Lys Asn Thr Ser Ala His Phe Leu Pro Met Val Val His Ser
                195                 200                 205 tag                                                                    627
```

<210> SEQ ID NO 2
<211> LENGTH: 208
<212> TYPE: PRT
<213> ORGANISM: Homo sapiens

<400> SEQUENCE: 2

```
Met Trp Lys Trp Ile Leu Thr His Cys Ala Ser Ala Phe Pro His Leu
 1               5                  10                  15

Pro Gly Cys Cys Cys Cys Cys Phe Leu Leu Leu Phe Leu Val Ser Ser
                20                  25                  30

Val Pro Val Thr Cys Gln Ala Leu Gly Gln Asp Met Val Ser Pro Glu
            35                  40                  45

Ala Thr Asn Ser Ser Ser Ser Ser Phe Ser Ser Pro Ser Ser Ala Gly
        50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205
```

<210> SEQ ID NO 3
<211> LENGTH: 35
<212> TYPE: DNA
<213> ORGANISM: Homo sapiens

<400> SEQUENCE: 3
ggaccctcat gacctgccag gctctgggtc aggac                                 35

<210> SEQ ID NO 4
<211> LENGTH: 28
<212> TYPE: DNA
<213> ORGANISM: Homo sapiens

```
<400> SEQUENCE: 4
ggacagccat ggctggtcgt cacgttcg                                28

<210> SEQ ID NO 5
<211> LENGTH: 29
<212> TYPE: DNA
<213> ORGANISM: Homo sapiens

<400> SEQUENCE: 5
ggacagccat ggttcgttgg cgtaaactg                               29

<210> SEQ ID NO 6
<211> LENGTH: 31
<212> TYPE: DNA
<213> ORGANISM: Homo sapiens

<400> SEQUENCE: 6
ggacagccat ggaaaaaaac ggtaaagttt c                            31

<210> SEQ ID NO 7
<211> LENGTH: 29
<212> TYPE: DNA
<213> ORGANISM: Homo sapiens

<400> SEQUENCE: 7 ggaccccat ggagaactgc ccgtagagc                                29

<210> SEQ ID NO 8
<211> LENGTH: 32
<212> TYPE: DNA
<213> ORGANISM: Homo sapiens

<400> SEQUENCE: 8 ggaccccat ggtcaaagcc attaacagca ac                            32

<210> SEQ ID NO 9
<211> LENGTH: 33
<212> TYPE: DNA
<213> ORGANISM: Homo sapiens

<400> SEQUENCE: 9 ggaccccat ggggaaactc tatggctcaa aag                           33

<210> SEQ ID NO 10
<211> LENGTH: 37
<212> TYPE: DNA
<213> ORGANISM: Homo sapiens

<400> SEQUENCE: 10
ctgcccaagc ttattatgag tgtaccacca ttggaag                      37

<210> SEQ ID NO 11
<211> LENGTH: 36
<212> TYPE: DNA
<213> ORGANISM: Homo sapiens

<400> SEQUENCE: 11
ctgcccaagc ttattacttc agcttacagt cattgt                       36

<210> SEQ ID NO 12
<211> LENGTH: 32
<212> TYPE: DNA
<213> ORGANISM: Homo sapiens
```

<400> SEQUENCE: 12
gcggcacatg tcttacaacc acctgcaggg tg                                    32

<210> SEQ ID NO 13
<211> LENGTH: 28
<212> TYPE: DNA
<213> ORGANISM: Homo sapiens

<400> SEQUENCE: 13
gggcccaagc ttatgagtgt accaccat                                          28

<210> SEQ ID NO 14
<211> LENGTH: 36
<212> TYPE: DNA
<213> ORGANISM: Homo sapiens

<400> SEQUENCE: 14
ccggcggatc ccatatgtct tacaaccacc tgcagg                                36

<210> SEQ ID NO 15
<211> LENGTH: 35
<212> TYPE: DNA
<213> ORGANISM: Homo sapiens

<400> SEQUENCE: 15
ccggcggtac cttattatga gtgtaccacc attgg                                 35

<210> SEQ ID NO 16
<211> LENGTH: 426
<212> TYPE: DNA
<213> ORGANISM: Homo sapiens

<400> SEQUENCE: 16
atgtcttaca accacctgca gggtgacgtt cgttggcgta aactgttctc tttcaccaaa      60
tacttcctga aaatcgaaaa aaacggtaaa gtttctggga ccaagaagga gaactgcccg     120
tacagcatcc tggagataac atcagtagaa atcggagttg ttgccgtcaa agccattaac     180
agcaactatt acttagccat gaacaagaag gggaaactct atggctcaaa agaatttaac     240
aatgactgta agctgaagga gaggatagag gaaaatggat acaataccta tgcatcattt     300
aactggcagc ataatgggag gcaaatgtat gtggcattga atggaaaagg agctccaagg     360
agaggacaga aaacacgaag gaaaaacacc tctgctcact tcttccaat ggtggtacac      420 tcataa                                                                426

<210> SEQ ID NO 17
<211> LENGTH: 141
<212> TYPE: PRT
<213> ORGANISM: Homo sapiens

<400> SEQUENCE: 17

Met Ser Tyr Asn His Leu Gln Gly Asp Val Arg Trp Arg Lys Leu Phe
 1               5                  10                  15

Ser Phe Thr Lys Tyr Phe Leu Lys Ile Glu Lys Asn Gly Lys Val Ser
            20                  25                  30

Gly Thr Lys Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr
    50                  55                  60

```
Leu Ala Met Asn Lys Lys Gly Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Arg Lys
        115                 120                 125

Asn Thr Ser Ala His Phe Leu Pro Met Val Val His Ser
    130                 135                 140
```

<210> SEQ ID NO 18
<211> LENGTH: 20
<212> TYPE: DNA
<213> ORGANISM: Homo sapiens

<400> SEQUENCE: 18
caaccacctg cagggtgacg                                          20

<210> SEQ ID NO 19
<211> LENGTH: 78
<212> TYPE: DNA
<213> ORGANISM: Homo sapiens

<400> SEQUENCE: 19
aacggtcgac aaatgtatgt ggcactgaac ggtaaaggtg ctccacgtcg tggtcagaaa    60
acccgtcgta aaacacc                                             78

<210> SEQ ID NO 20
<211> LENGTH: 76
<212> TYPE: DNA
<213> ORGANISM: Homo sapiens

<400> SEQUENCE: 20
gggcccaagc ttaagagtgt accaccattg gcagaaagtg agcagaggtg tttttacgac    60
gggttttctg accacg                                              76

<210> SEQ ID NO 21
<211> LENGTH: 23
<212> TYPE: DNA
<213> ORGANISM: Homo sapiens

<400> SEQUENCE: 21
gccacataca tttgtcgacc gtt                                      23

<210> SEQ ID NO 22
<211> LENGTH: 19
<212> TYPE: DNA
<213> ORGANISM: Homo sapiens

<400> SEQUENCE: 22
gggcccaagc ttaagagtg                                           19

<210> SEQ ID NO 23
<211> LENGTH: 23
<212> TYPE: DNA
<213> ORGANISM: Homo sapiens

<400> SEQUENCE: 23
gccacataca tttgtcgacc gtt                                      23

<210> SEQ ID NO 24
<211> LENGTH: 90
<212> TYPE: DNA
<213> ORGANISM: Homo sapiens

<400> SEQUENCE: 24

```
ctgcagggtg acgttcgttg gcgtaaactg ttctccttca ccaaatactt cctgaaaatc      60
gaaaaaaacg gtaaagtttc tggtaccaag                                      90
```

<210> SEQ ID NO 25
<211> LENGTH: 90
<212> TYPE: DNA
<213> ORGANISM: Homo sapiens

<400> SEQUENCE: 25

```
agctttaaca gcaacaacac cgatttcaac ggaggtgatt tccaggatgg agtacgggca      60
gttttctttc ttggtaccag aaactttacc                                      90
```

<210> SEQ ID NO 26
<211> LENGTH: 90
<212> TYPE: DNA
<213> ORGANISM: Homo sapiens

<400> SEQUENCE: 26

```
ggtgttgttg ctgttaaagc tatcaactcc aactactacc tggctatgaa caagaaaggt      60
aaactgtacg gttccaaaga atttaacaac                                      90
```

<210> SEQ ID NO 27
<211> LENGTH: 100
<212> TYPE: DNA
<213> ORGANISM: Homo sapiens

<400> SEQUENCE: 27

```
gtcgaccgtt gtgctgccag ttgaaggaag cgtaggtgtt gtaaccgttt tcttcgatac      60
gttctttcag tttacagtcg ttgttaaatt ctttggaacc                           100
```

<210> SEQ ID NO 28
<211> LENGTH: 25
<212> TYPE: DNA
<213> ORGANISM: Homo sapiens

<400> SEQUENCE: 28

```
gcggcgtcga ccgttgtgct gccag                                           25
```

<210> SEQ ID NO 29
<211> LENGTH: 26
<212> TYPE: DNA
<213> ORGANISM: Homo sapiens

<400> SEQUENCE: 29

```
gcggcctgca gggtgacgtt cgttgg                                          26
```

<210> SEQ ID NO 30
<211> LENGTH: 36
<212> TYPE: DNA
<213> ORGANISM: Homo sapiens

<400> SEQUENCE: 30

```
ccggcggatc ccatatgtct tacaaccacc tgcagg                               36
```

```
<210> SEQ ID NO 31
<211> LENGTH: 34
<212> TYPE: DNA
<213> ORGANISM: Homo sapiens

<400> SEQUENCE: 31
cgcgcgatat cttattaaga gtgtaccacc attg                                34

<210> SEQ ID NO 32
<211> LENGTH: 426
<212> TYPE: DNA
<213> ORGANISM: Homo sapiens

<400> SEQUENCE: 32
atgtcttaca accacctgca gggtgacgtt cgttggcgta aactgttctc cttcaccaaa    60
tacttcctga aatcgaaaa aaacggtaaa gtttctggta ccaagaaaga aaactgcccg   120
tactccatcc tggaaatcac ctccgttgaa atcggtgttg ttgctgttaa agctatcaac   180
tccaactact acctggctat gaacaagaaa ggtaaactgt acggttccaa agaatttaac   240
aacgactgta aactgaaaga acgtatcgaa gaaaacggtt acaacaccta cgcttccttc   300
aactggcagc acaacggtcg acaaatgtat gtggcactga acggtaaagg tgctccacgt   360
cgtggtcaga aacccgtcg taaaaacacc tctgctcact ttctgccaat ggtggtacac   420
tcttaa                                                             426

<210> SEQ ID NO 33
<211> LENGTH: 141
<212> TYPE: PRT
<213> ORGANISM: Homo sapiens

<400> SEQUENCE: 33

Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
     50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Arg Lys
        115                 120                 125

Asn Thr Ser Ala His Phe Leu Pro Met Val Val His Ser
    130                 135                 140
```